(12) United States Patent
Cameron et al.

(10) Patent No.: US 9,076,107 B2
(45) Date of Patent: Jul. 7, 2015

(54) NEURAL NETWORK SYSTEM AND USES THEREOF

(71) Applicant: The University of Toledo, Toledo, OH (US)

(72) Inventors: Brent D. Cameron, Waterville, OH (US); Scott M. Pappada, Cleveland Heights, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/284,975

(22) Filed: May 22, 2014

(65) Prior Publication Data

US 2014/0304204 A1    Oct. 9, 2014

Related U.S. Application Data

(62) Division of application No. 13/058,673, filed as application No. PCT/US2009/053943 on Aug. 14, 2009, now Pat. No. 8,762,306.

(60) Provisional application No. 61/088,958, filed on Aug. 14, 2008.

(51) Int. Cl.
*G06F 19/00* (2011.01)
*G06F 15/18* (2006.01)
*G06N 3/08* (2006.01)

(52) U.S. Cl.
CPC .............. *G06N 3/08* (2013.01); *G06F 19/3437* (2013.01); *G06F 19/345* (2013.01); *G06F 19/3456* (2013.01)

(58) Field of Classification Search
None
See application file for complete search history.

(56) References Cited

U.S. PATENT DOCUMENTS

| | | | |
|---|---|---|---|
| 5,103,496 A | 4/1992 | Andes et al. | |
| 5,633,954 A * | 5/1997 | Gupta et al. | ............... 382/187 |
| 5,727,128 A | 3/1998 | Morrison | |
| 6,272,480 B1 * | 8/2001 | Tresp et al. | ................... 706/44 |
| 6,379,301 B1 | 4/2002 | Worthington et al. | |
| 6,544,212 B2 | 4/2003 | Galley et al. | |
| 6,572,545 B2 | 6/2003 | Knobbe et al. | |
| 6,582,366 B1 | 6/2003 | Porumbescu | |
| 6,601,053 B1 | 7/2003 | Schaffer et al. | |
| 6,658,396 B1 | 12/2003 | Tang et al. | |

(Continued)

FOREIGN PATENT DOCUMENTS

| | | |
|---|---|---|
| KR | 1019980025157 A | 7/1998 |
| WO | 2007149533 A2 | 12/2007 |

(Continued)

OTHER PUBLICATIONS

Ivanov et al., "Temporal Processing Neural Networks for Speech Recognition", International Conference on Neural Networks and Artificial Intelligence, 1999, pp. 1991-1999.

(Continued)

*Primary Examiner* — Jeffrey A Gaffin
*Assistant Examiner* — Mikayla Chubb
(74) *Attorney, Agent, or Firm* — MacMillan, Sobanski & Todd, LLC

(57) ABSTRACT

A multifunctional neural network system for prediction which includes memory components to store previous values of data within a network. The memory components provide the system with the ability to learn relationships/patterns existent in the data over time.

25 Claims, 9 Drawing Sheets

(56) References Cited

U.S. PATENT DOCUMENTS

| | | |
|---|---|---|
| 6,882,940 B2 | 4/2005 | Potts et al. |
| 6,923,763 B1 | 8/2005 | Kovatchev et al. |
| 6,931,327 B2 | 8/2005 | Goode, Jr. et al. |
| 7,025,425 B2 | 4/2006 | Kovatchev et al. |
| 7,052,472 B1 | 5/2006 | Miller et al. |
| 7,230,529 B2 | 6/2007 | Ketcherside, Jr. et al. |
| 7,296,005 B2* | 11/2007 | Minamino et al. ............ 706/15 |
| 8,762,306 B2 | 6/2014 | Cameron et al. |
| 2003/0153821 A1* | 8/2003 | Berner et al. ............ 600/345 |
| 2003/0175806 A1* | 9/2003 | Rule et al. ............ 435/7.1 |
| 2004/0167418 A1 | 8/2004 | Nguyen et al. |
| 2005/0119534 A1 | 6/2005 | Trost et al. |
| 2005/0119540 A1* | 6/2005 | Potts et al. ............ 600/315 |
| 2005/0197554 A1 | 9/2005 | Polcha |
| 2006/0264718 A1* | 11/2006 | Ruchti et al. ............ 600/310 |
| 2007/0032706 A1* | 2/2007 | Kamath et al. ............ 600/300 |
| 2007/0208246 A1* | 9/2007 | Brauker et al. ............ 600/365 |
| 2008/0027292 A1* | 1/2008 | Rosman et al. ............ 600/300 |
| 2008/0033254 A1 | 2/2008 | Kamath et al. |
| 2008/0082323 A1 | 4/2008 | Bai et al. |
| 2008/0189051 A1* | 8/2008 | Goode et al. ............ 702/22 |
| 2008/0221923 A1 | 9/2008 | Shogan |
| 2009/0105573 A1* | 4/2009 | Malecha ............ 600/365 |
| 2009/0156924 A1* | 6/2009 | Shariati et al. ............ 600/365 |
| 2009/0177143 A1* | 7/2009 | Markle et al. ............ 604/66 |
| 2009/0192366 A1* | 7/2009 | Mensinger et al. ............ 600/301 |
| 2009/0192722 A1* | 7/2009 | Shariati et al. ............ 702/19 |
| 2010/0280348 A1* | 11/2010 | Wenzel et al. ............ 600/365 |
| 2010/0291604 A1* | 11/2010 | Rosman et al. ............ 435/14 |
| 2010/0292634 A1* | 11/2010 | Kircher et al. ............ 604/66 |
| 2011/0225112 A1 | 9/2011 | Cameron et al. |
| 2014/0304204 A1 | 10/2014 | Cameron et al. |

FOREIGN PATENT DOCUMENTS

| | | |
|---|---|---|
| WO | 2008131224 A2 | 10/2008 |
| WO | 2010019919 A1 | 2/2010 |

OTHER PUBLICATIONS

Magoulas et al., "Effective Backpropagation Training with Variable Stepsize", Neural Networks, 1997, vol. 10, No. 1, pp. 69-82.

Pappada et al., "Neural Network Prediction of Glucose in Diabetic Patients Using Continuous Glucose Monitoring (CGM) and an Electronic Intensive Life Event Diary (EILED)", 2006, Department of Bioengineering, University of Toledo, Toledo, Ohio and Northeastern Ohio Universities of College of Medicine, Rootstown, Ohio, one (1) page poster.

Prank et al., "Predictive Neural Networks for Learning the Time Course of Blood Glucose Levels from the Complex Interaction of Counterregulatory Hormones", Neural Computation, 1998, vol. 10, pp. 941-953.

Skevofilakas et al., "A Communication and Information Technology Infrastructure for Real Time Monitoring and Management of Type I Diabetes Patients", Engineering in Medicine and Biology Society, 2007, pp. 3685-3688.

PCT International Search Report and Written Opinion, Application No. PCT/US2009/053943 filed Aug. 14, 2009, dated Dec. 24, 2009.

PCT International Preliminary Report on Patentability, Application No. PCT/US2009/053943 filed Aug. 14, 2009, dated Feb. 24, 2011.

PCT International Search Report and Written Opinion, Application No. PCT/US2013/063178 filed Oct. 3, 2013, dated Jan. 28, 2014, 15 pages.

* cited by examiner

| Table 1. Performance Analysis on Unseen Data: Variation of Training Set Length (100 minute Predictive Window) ||
|---|---|
| Number of Patients | Overall MAD(%) |
| 11 | 18.7 |
| 14 | 25.8 |
| 17 | 22.5 |

| Table 2. Performance Analysis: Unseen Data With Predictive Window Variation ||
| :---: | :---: |
| Predictive Window | Overall MAD(%) |
| 50 min | 6.7 |
| 100 min | 11.7 |
| 180 min | 18.9 |

NEURAL NETWORK SYSTEM AND USES THEREOF

CROSS-REFERENCE TO RELATED APPLICATIONS AND STATEMENT REGARDING SPONSORED RESEARCH

The present invention is a divisional application of U.S. Ser. No. 13/058,673, filed Feb. 24, 2011, which claims the benefit of the PCT/US2009/053943 filed Aug. 14, 2009, which claims priority to the provisional patent application Ser. No. 61/088,958 filed Aug. 14, 2008. This invention was not made with any government support and the government has no rights in this invention.

BACKGROUND OF THE INVENTION

There is no admission that the background art disclosed in this section legally constitutes prior art.

Type I diabetes is an autoimmune disease in which the beta-cells of the body are destroyed thus resulting in a lack of insulin production. This leads to an inability to control blood glucose concentration as insulin facilitates the cellular uptake of glucose. If levels of blood glucose concentration remain high for extended periods of time, long-term complications such as neuropathy, nephropathy, vision loss and the like can arise. Due to the lack of insulin production, type I diabetics are required to take insulin subcutaneously as their primary method of therapy.

The major difficulty involving the successful treatment of diabetes is the appropriate dosing of insulin such that a normal physiologic glucose concentration is maintained. There are a multitude of factors which influence subsequent glucose concentrations in diabetics including but not limited to: insulin dosage, carbohydrate and nutritional intake, lifestyle (i.e., sleep-wake cycles and sleep quality, exercise, etc.), and emotional states (i.e., stress, depression, contentment, etc.). The effect of these various factors on subsequent glucose levels is not fully understood, and may be similar across all diabetic patients or patient specific. In order to optimize control in diabetic patients, there needs to be some method for quantifying or predicting future occurrences of dysglycemia (i.e., high and low blood glucose concentration, also referred to as hyperglycemia and hypoglycemia, respectively).

Fluctuations in glucose concentration experienced on an everyday basis appear to be chaotic, however, prior research does elude to possible patterns which may exist. Circadian rhythms in sleep and subsequent glucose regulation have been identified in previous research. Other patterns in insulin activity, insulin sensitivity, and their subsequent effect on glucose concentration have been identified in previous research. The existence of rhythms in insulin activity, and subsequent quantifiable patterns in glucose fluctuations, provide the foundation and construct for the development of the neural network models described herein.

The advent of continuous glucose monitoring (CGM) in the field of diabetes technology provides even more insight for the determination of patterns existent in daily glucose fluctuations of diabetic patients. The usage of CGM technology is also advantageous as it leads to a better understanding of gluco-regulatory dynamics.

Attempts to model blood glucose and insulin interactions in diabetic individuals have been an ongoing topic in current research. The complexity of the neural networks developed in such studies range from simplistic feed-forward neural networks to more complex recurrent networks. In most of these studies, in an attempt to achieve tight glucose control in the normal physiological range, a controller is used to determine the required insulin dosage (based on glucose prediction). The determination of optimal insulin dosages is likely to have considerable error associated with each model as each patient possesses different insulin sensitivities.

In many of the previous endeavors aimed at predicting glucose or optimal insulin dosages to maintain normal glucose concentration, models were generated using inputs including: glucose meter readings, insulin dosages, exercise/activity status, and nutritional intake. While these factors undoubtedly contribute to changes in blood glucose concentration and are quantifiable, there are many factors which are left unrecognized in previous models, particularly other lifestyle and emotional factors.

As mentioned previously, a major difficulty in the management of diabetes is the optimization of insulin therapies to avoid occurrences of hypoglycemia and hyperglycemia. The overall effect of the factors impacting glucose fluctuations has not been fully quantified to determine the impact on subsequent glycemic trends.

The recent advances in diabetes technology such as real-time continuous glucose monitoring (CGM) provide significant sources of data such that quantification may be possible. Depending on the CGM technology utilized, the sampling frequency ranges from 1-5 minutes.

However, physiological systems and diseases, such as diabetes mellitus which affect such systems, are extremely complex in nature. Attempts to analyze and better understand these types of "systems" have utilized methods such as control engineering. Based on these methods, there have been many attempts aimed at prediction, simulation, and fault detection. Although these methods, in part, provide insight into biological systems, they are still limited due to the inherent complexity of the systems they are attempting to model.

An Artificial Neural Network (ANN) is one approach that is recently gaining considerable interest. In part, this is due to its inherent nature which would seem to be well suited to model complex physiological systems. An ANN functions as a brain within a nervous system, in that it has the ability to distinguish and recognize a particular object from a large set of objects. Neural networks can be utilized to construct a mathematical model of a specific system which is to be controlled.

Another application for the development of such systems which has not received considerable research attention, is in reducing post-traumatic hyperglycemia. Following severe trauma, research indicates that approximately 5% of individuals may experience hyperglycemia. If hyperglycemia is sustained, mortality and requirements for care are potentially increased. Published data indicate that lowering glucose levels after trauma may decrease mortality, the length of stay on ventilators, incidence of infection, and length of stay in the intensive care unit (ICU) and in the hospital. Aggressive therapy to maintain glucose levels below 150 mg % was shown to improve outcomes although the ability to sustain this goal in post-traumatic circumstances may be difficult as the patient recovers.

Continuous glucose monitoring (CGM) in a real-time setting represents a tremendous advantage in such a venue. CGM allows for the assessment of trends in glycemic excursions over an extended period of time. CGM in patients, who have sustained significant trauma, combined with a system capable of anticipating post-traumatic hyperglycemia, may enhance glycemic control and reduce post-trauma glycemic variability, thus potentially reducing infection rates, ventilator days, pneumonia, length of stay in the ICU, and mortality. For example, if glucose levels exceed 200 mg % in several injured patients on admission to trauma centers, their expected survival has been reported to be reduced by more than 50%. Persistence of this hyperglycemia during the first 2 days after trauma has been shown to further reduce survival and increasing glucose levels during this early post-trauma period has been shown to potentially predict adverse outcomes in these patients. Glucose levels greater than 150 mg % during the first 2 post-trauma days is also associated with an increased risk of mortality and/or other complications and subsequent euglycemic maintenance does not appear to improve these outcomes.

Post-traumatic hyperglycemia is a significant health risk and occurs with a relative high frequency. In an unpublished study at the University of Toledo Medical Center, measurements of the initial glucose concentration of 50 Level 1 trauma patients were obtained upon arrival to the critical care unit. Of these, 53% had elevated glucose concentrations (≥150 mg/dL). Of these patients, 34% had glycemic levels within 150-199 mg/dL and were defined as elevated and 19% had glucose concentrations greater than 199 mg/dL and were defined as highly elevated; results of this study are summarized in FIG. 1.

Patients with initial glucose concentrations≥150 mg/dL usually experienced considerable glycemic variability over the course of their stay in the critical care unit.

FIG. 2 illustrates the degree of glycemic variability in a single trauma patient over the course of their stay in the intensive care unit and demonstrates the need for intervention to maintain glucose levels in a normal range.

To minimize the incidence of hyperglycemia following trauma, prompt, aggressive, and sustained treatment is needed, especially to reduce development of adverse outcomes.

Another application for the utilization and development of such predictive systems for glucose include cardio-thoracic surgical patients and other critical care patients which commonly experience elevated glucose. While models for these patients have generated little research attention, the research conducted demonstrates the need for glycemic prediction and optimization of glycemic control in this patient base. For example, patients who undergo some form of cardiovascular surgical intervention are also prone to glycemic fluctuations. Control of glucose concentration in such patients is a desired goal for improving patient outcomes. Also, tight glycemic control in cardiac surgical patients has been correlated to reduced morbidity and mortality rates. Thus, it is integral to patient outcome, that tight glycemic control be obtained in cardiac surgical patients both interoperatively/perioperatively as well as post operatively.

In other venues, such as in a military situation, with current technology, the intervention required is likely to exceed the capability of medics in the field. The ability to make key decisions, such as rapid evacuation or for individuals in remote places where evacuation can be difficult or dangerous, the need for aggressive treatment becomes a critical judgment. There is a need to provide improved monitoring technology and treatment criteria, as well as, rapid and accurate assessment of the appropriate urgency for treatment of the wounded.

In addition, recent research includes:

U.S. Pat. No. 7,052,472: Systems and methods for detecting symptoms of hypoglycemia;

U.S. Pat. No. 7,025,425: Method, system, and computer program product for the evaluation of glycemic control in diabetes from self-monitoring data;

U.S. Pat. No. 6,931,327: System and methods for processing analyte sensor data;

U.S. Pat. No. 6,923,763: Method and apparatus for predicting the risk of hypoglycemia;

U.S. Pat. No. 6,882,940: Methods and devices for prediction of hypoglycemic events:

U.S. Pat. No. 6,658,396: Neural network drug dosage estimation;

U.S. Pat. No. 6,582,366: Medical devices for contemporaneous decision support in metabolic control;

U.S. Pat. No. 6,572,535: Method and apparatus for real-time control of physiological parameters;

U.S. Pat. No. 6,572,542: System and method for monitoring and controlling the glycemic state of a patient;

U.S. Pat. No. 6,544,212: Diabetes management system;

U.S. Pat. No. 6,379,301: Diabetes management system and method for controlling blood glucose;

U.S. Pat. No. 6,272,480: Method and arrangement for the neural modeling of a dynamic system with non-linear stochastic behavior; and U.S. Pat. No. 7,230,529: System, method, and computer program for interfacing an expert system to a clinical information system.

Therefore, what is needed is an improved supporting algorithm and model for glycemic forecasting and prediction for use with glucose monitoring technologies.

There is a need for improved predictive models for glucose which do not have the prior systems' significant prediction error and limited prediction windows of a few minutes.

It is also desired to have a system that utilizing these glycemic predictions provides the ability to determine insulin dosage estimates for maintaining normal glucose concentration utilizing an algorithm/model which has the capability to learn and adapt given historical trends in glycemic data.

It is further desired to provide a system that has patient/user interaction. The patient and user should be able to select the predictive/forecast window. Such a system should be configured to alert/alarm the user/patient in the event that dysglcyemia (hypoglycemia and hyperglycemia) are predicted, or the system estimates there is a high probability of the occurrence of these unwanted glycemic states.

SUMMARY OF THE INVENTION

In a first broad aspect, there in provided herein a neural network system, comprising the following elements: i) an input layer designed to accept N inputs; ii) one or more "i" hidden layers, iii) an output layer; iv) at least one neuron "$Y_{layer}$" within each layer, where "layer" is the layer defined as "input", "hiddeni" or "output"; and, v) one or more memory structures configured to: a) store a recursive memory of input signals past, and b) allow for at least one time series prediction of a response.

In certain embodiments, the neural network system is a time-lagged feed forward neural network system for predicting analyte levels in a sample or a subject in need thereof.

In certain embodiments, one or more memory structures are included in both the input and hidden layers.

In certain embodiments, the neural network system further includes one or more memory structures included in the output layer.

In certain embodiments, the input layer being configured to accept and store at least one memory of a current input signal and at least one memory of a previous input signal, the input layer also being configured to: store a record of the input signals past, and provide a usable history of previous input data to allow at least one time series prediction.

In certain embodiments, the neural network is configured to predict a complete vector of predicted values with a respective time vector t, wherein the complete vector of predicted values comprises all predicted values up to n minutes desired predictive window, and wherein the respective time vector t is adaptive to accommodate a defined sampling rate (Δt).

In certain embodiments, the hidden layers have one or more $Y_{hiddeni}$ neurons/processing elements configured for providing an alternative representation of input data, and, optionally, configured for simplifying the input data to a specific range of values in order to enhance a training/learning process of the neural network system.

In certain embodiments, the $Y_{hiddeni}$ hidden layer neurons/processing elements are configured to utilize one or more transfer functions selected from: hyperbolic tangent, sigmoid, and linear functions.

In certain embodiments, at least one hidden layer contains at least one memory structures $MD_{hiddeni}$ configured to: store a record of the input signals past, and provide a usable history of previous input data to allow for at least one time series prediction.

In certain embodiments, the output layer has one or more $Y_{output}$ processing elements/neurons configured for implementing at least one transfer function. In certain embodiments, at least one transfer function is implemented in the hidden layer.

In certain embodiments, at least one $Y_{output}$ processing element is configured to output a predicted response in a format of a desired output of the neural network system.

In certain embodiments, the number of neurons/processing elements ($Y_{output}$) in the output layer is the same as a desired number of outputs of the neural network system.

In certain embodiments, the neural network system is configured to be trained via a backpropagation algorithm having one or more elements $BP^{layer}$ in the neural network system help facilitate a training process, where "layer" is the layer(s) defined as "input", "hiddeni" and "output" to which the $BP^{layer}$ corresponds.

In certain embodiments, one or more $BP^{layer}$ elements derive a relative error at their input which is to be back propagated to any processing elements which precede them in the neural network system.

In certain embodiments, the back propagation of errors is completed as an error and is presented at the output of each $BP^{layer}$ element, wherein each $BP^{layer}$ element is charged with calculating gradient information associated with calculating weights for minimization of total error in the neural network system.

In certain embodiments, optimal weights for minimization of error are obtained via a gradient descent algorithm performed within each $BP^{layer}$ element. In certain embodiments, the optimal weights calculated via the gradient descent algorithm are changed in the elements and synapses/connections between a current and next layer of the neural network system, whereby the weighted inputs are summed at the input of each neuron/processing element.

In certain embodiments, the gradient descent algorithm calculates the optimal weights for minimization of total error in the neural network system by specifying a step size in which the algorithm iterates to determine a local minimum.

In certain embodiments, the neural network is configured to utilize momentum to aid in the gradient descent algorithm, wherein momentum provides the gradient descent algorithm inertia such that the algorithm continues to move along the average estimate for down in its search for a local minimum.

In certain embodiments, the neural network system is configured to be trained via batch training approach.

In certain embodiments, network weights are updated after/during each epoch, wherein the epoch comprises a single cycle/pass through a dataset.

In certain embodiments, the neural network system is configured to stop training if a calculated mean squared error was less than a specified threshold or after n epochs.

In certain embodiments, the neural network system is trained via an optimization technique.

In certain embodiments, the optimization technique comprises a genetic algorithm configured to minimize the number of processing elements (neurons) and inputs into the neural network system.

In certain embodiments, the genetic algorithm is configured to determine which inputs have an impact on predictions and to minimize various interconnections between neurons in the neural network system.

In certain embodiments, wherein the genetic algorithm determines one or more optimum values for step-size and momentum to minimize the time required for weight optimization and training via a gradient search algorithm. In certain embodiments, N inputs in the input layer are pre-processed to decrease the time needed for training/executing the neural network system and to increase the predictive accuracy of the neural network system.

In certain embodiments, the neural network is configured to further include pre-processing of data such that new inputs experienced by the neural network system are taken into account, and model weights and normalization of input values are modified as the new input data is presented to the neural network system.

In certain embodiments, the pre-processing of inputs to the neural network system is completed using one or more algorithmic techniques selected from: normalization and weighting.

In certain embodiments, the neural network system is configured for both real-time prediction and retrospective prediction.

One or more support/post processing algorithms are included in order to modify the neural network system predictive output such that an increased predictive accuracy is achieved.

In certain embodiments, the neural network includes one or more support/post processing algorithms selected from: an adaptive analyte threshold based rate of change (ROC) algorithm and input variable, or event, oriented trend analysis algorithm.

In certain embodiments, the adaptive analyte threshold based ROC post processing algorithm is configured to track the ROC of analyte data presented to the neural network system.

In certain embodiments, based on a current analyte value and ROC of current and previous analyte values, if the n predicted analyte values do not correlate with the ROC, the predicted output of the neural network system are modified via the post processing algorithm to increase predictive accuracy.

In certain embodiments, the post processing includes an adaptive analyte threshold based ROC approach:

$$ROC(t) = \frac{(CGM_t - CGM_{t-1})}{\Delta t}, \qquad \text{Equation [1]}$$

wherein
$CGM_t$ is the current real-time value,
$CGM_{t-1}$ is the previous value, Δt is the time duration between the two samples or sampling rate of a monitoring device, and ROC(t) is the real-time ROC, wherein, n predicted values generated are adjusted to coordinate with real-time ROC to enhance predictive accuracy via Equation [2], $$PREDICT_{mod} = PREDICT_{CGM} + W_{ROC} \cdot ROC \cdot \Delta t \quad \text{Equation [2]},$$

wherein, $PREDICT_{CGM}$ is a vector of predicted CGM values with length n, $W_{ROC}$ is a vector of length n of weights for weighting ROC values based on the current real-time value (threshold) and is adaptable via various mathematical approaches, $ROC_{predict}$ is a vector of ROC values of length n estimated based on best linear, or nonlinear model of real-time ROC, Δt is a time duration between the two samples or a sampling rate, and $PREDICT_{mod}$ is a vector of modified (post-processed) predictions to increase accuracy based on trends in real-time ROC.

In certain embodiments, the neural network is configured to include one or more input variables oriented trend analysis post processing algorithms which are configured to analyze one or more predicted outputs of the neural network system for one or more expected trends in predicted analyte values based on previous and current input data presented to the neural network system.

In certain embodiments, at least one trend is quantifiable and is programmed into the neural network system to gauge if predictions generated by the neural network system are accurate. For example, in certain embodiments, if predictions digress from an expected trend, appropriate post-processing is completed to modify predictions and enhance predictive accuracy. Also, the expected trend does not occur in n predicted values, then the post processing algorithm can modify the neural network system output to increase predictive accuracy.

In certain embodiments, analyte can comprise one or more of: naturally occurring, artificial, metabolites, and/or reaction products. In certain embodiments, the analyte can comprises one or more of: glucose; blood and/or urine components; proteins; amino acids; hormones; cholesterol; viruses; toxins; antibodies; antigens; vitamins; imaging contrast agents; illegal drugs; pharmaceutical compositions; and steroids.

In certain embodiments, one or more of the input signals past comprise: physiologic, emotional, lifestyle, medication, and nutritional factors, factors documented during the course of the subject's normal everyday life, or during treatment, stay in intensive care or other supervised setting, and medical records. For example, in certain embodiments, at least one trend includes: an increase in glucose followed by a decrease to normal levels if a medication dosage was sufficient.

In certain embodiments, the neural network system is configured to be used prospectively and retrospectively to gauge at least one change and/or at least one occurrence of one or more input factors and a corresponding effect of the factors on at least one prediction.

In certain embodiments, the neural network system is configured for use as a retrospective and/or prospective iterative therapeutic and/or educational tool for determination of effect of at least one input variable on predicted outputs which include, but are not limited to: analyte concentration, analyte state, and analyte dependent outcomes.

In certain embodiments, at least one input variable comprises one or more of: analyte concentration, analyte levels, analyte states and outcomes.

Also provided herein is the use of the multi-functional neural network system for monitoring one or more of: type I and type II diabetes, hospital/critical care/trauma patients/cardio-thoracic surgical patients, and military personnel.

In certain embodiments, the neural network system can be configured for predicting one or more outputs selected from: glucose levels, including discrete and/or CGM values; glucose states, including classified ranges of glucose values; glycated hemoglobin A1C values, mortality, morbidities, and complications; at a point in time n minutes in the future, when applicable, in real-time and retrospectively.

Also, the neural network system can be configured for providing administration of insulin/medication dosage administration, and intelligent therapy guidance, in an integrated or stand-alone manner.

In another broad aspect, there is provided herein a modeling/predictive system comprising: predicting glucose levels in a subject in need thereof using a neural network.

In another broad aspect, there is provided herein a method for intelligent therapy recommendation/semi-closed loop insulin/medication infusion, comprising: providing a prediction of glucose levels in a subject, and determining one or more of: insulin/medication dosage administration, outcomes pertinent thereto and/or intelligent therapy guidance, in an integrated manner.

In another broad aspect, there is provided herein a system for forecasting one or more of: elevated glucose levels and/or lack of optimal glycemic control, in a subject in need thereof, comprising using the neural network described herein.

In certain embodiments, the subject is selected from one or more of: patients with type I/II diabetes, trauma patients, critical care patients, cardio-thoracic surgical patients, and military personnel.

In certain embodiments, the forecasts are used to improve or maintain blood glucose levels at near normal concentrations through active, therapeutic directions/assistance or automated therapy.

In another broad aspect, there is provided herein a multi-functional neural network system comprising memory components to store previous values of data within a network; the memory components providing the system with the ability to learn relationships/patterns existent in the data over time.

In certain embodiments, the neural network system is capable of being configured by a user to predict glucose n minutes ahead of time and to forecast glucose levels over a predetermined time in the future.

In certain embodiments, the neural network system is capable of being configured to use multiple inputs for prediction.

In certain embodiments, the multiple inputs include one or more of: time, meter glucose readings, nutritional intake, daily activities, lifestyle factors, emotional states, medication intake and patient medical records.

In certain embodiments, the neural network system can be configured to use multiple inputs for prediction utilizing continuous glucose monitoring (CGM) data.

In certain embodiments, the neural network system can be configured to use multiple inputs for prediction utilizing meter blood glucose data.

In certain embodiments, the neural network system can be configured to be trained via a backpropagation neural network training modality/algorithm.

In certain embodiments, the neural network system is capable of being trained via a batch training method.

In certain embodiments, the neural network system is capable of being trained via an optimization technique.

In certain embodiments, the neural network system can be configured for real-time and retrospective prediction.

In certain embodiments, the predictive capabilities of the neural network include pre-processing and support/post processing algorithms to modify neural network predictive output such that an increased predictive accuracy is achieved.

In certain embodiments, the post-processing/supporting algorithm is selected from: adaptive glycemic threshold based rate of change (ROC) algorithms, and input variable (event) oriented trend analysis algorithms.

In certain embodiments, the glycemic threshold based rate of change (ROC) post processing algorithm track real-time ROC of glucose data presented to the neural network.

In certain embodiments, the neural network includes one or more post processing algorithms configured to analyze predicted output of the neural network for expected trends in predicted glucose values based on previous and current input data presented to the neural network.

In certain embodiments, the neural network is configured to predict future glucose values and/or outcomes which provides a user with advanced knowledge in real-time of possible unwanted glycemic excursions and outcomes.

In certain embodiments, the neural network is configured to allow a user to select an amount of time to predict values ahead of time, and to display one or more of: current, previous history, and predicted output in real-time.

In certain embodiments, the neural network is configured with one or more alerts and/or alarms to alert a user of potential and present unwanted glucose values and outcomes.

In certain embodiments, the neural network is configured to calculate error in prediction and to retrain or reformulate at least one model weight for increased accuracy.

In certain embodiments, the neural network is configured to alerts a user when predictive accuracy is below a desirable error threshold, thereby allowing the user to interpret results using clinical judgment cautiously.

In certain embodiments, the neural network is configured to be used retrospectively to analyze an effect of medication and/or other input data on future predicted values such that appropriate modifications to therapy can be made.

In certain embodiments, the neural network is configured to provide a user with type I or type II diabetes with therapeutic guidance such that the user can make modifications to avoid unwanted glucose values and outcomes.

In certain embodiments, the neural network is configured to monitor patients in a hospital/critical care setting with elevated glucose.

In certain embodiments, the neural network is configured as monitor for monitoring real-time and predicted glucose in critical care and hospital patients, to alert, guide, and optimize glycemic control in critical care patients with lack of glycemic control.

In certain embodiments, the neural network is configured to gauge performance and status of military personnel on the battlefield.

In certain embodiments, the neural network is configured to be implemented in a closed loop system or a semi-closed loop system.

In certain embodiments, the neural network is configured to predict glucose and outcomes n minutes in the future as well as suggest therapeutic changes in medication for mitigation and prevention of unwanted glycemic excursions and outcomes.

In certain embodiments, the neural network is configured to allow a user to choose whether to accept any therapeutic recommendations given by the semi-closed loop system implementing the multifunctional neural network model, or modify the recommendations to adjust medication delivery.

In certain embodiments, the neural network is configured to be capable of being automatically integrated with a medication delivery system to allow changes in therapy desired by a user to be implemented in real-time.

In certain embodiments, the neural network is configured to be capable of being modified to function as a closed loop system to automatically deliver medication and other therapeutic changes to maintain desired glucose values and outcomes.

In certain embodiments, the neural network is configured to be used with one or more of: computers, smartphones, pocket PCs/PDAs, laptop/tablet PCS and PCs.

In certain embodiments, the neural network is configured to be integrated for used with one or more of: current and future glucose monitoring, insulin infusion technologies for prediction of glucose, outcomes, medication dosages/lifestyle changes needed for improved glycemic control, variables pertinent to optimization of glycemic control and outcome in patients with diabetes (type I and II), trauma/hospital/cardio-thoracic surgical patients/critical care, military personnel, and other patients with elevated glucose and lack of optimized glycemic control.

In certain embodiments, the neural network is configured to be used prospectively and retrospectively to gauge the changing or occurrence of various input factors and their corresponding effect on predictions of analyte concentration, outcome, analyte states.

In another broad aspect, there is provided herein a method for predicting analyte levels and medication dosages, comprising: i) providing a multifunctional neural network system for prediction of one or more of: analyte concentration values, analyte levels, analyte states, medication dosages, physiologic outcomes and clinical outcomes; ii) presenting pre-processing of input data to the neural network system; iii) providing a neural network system output post processing algorithm to enhance predictive accuracy during a time of decreased accuracy; iv) providing a capability for neural network system re-training for model weight optimization when new data combinations and results are experienced.

In another broad aspect, there is provided herein a method for predicting analyte levels in a subject in need thereof, comprising: i) providing for integration of real-time continuous monitoring data as an input and an output of a time lagged feed forward neural network system; and ii) using the neural network system of step i) to provide both previous and current real-time data in order to predict future real-time data trends. In certain embodiments, the method can further comprise the step of real-time data-logging of variables which may be predictors of future changes in analyte levels.

In another broad aspect, there is provided herein a method for providing a neural network, comprising: i) providing an input layer designed to accept N inputs; ii) providing one or more "i" hidden layers, iii) providing an output layer; iv) providing at least one neuron "Ylayer" within each layer, where "layer" is the layer defined as "input", "hiddeni" or "output"; and, v) providing one or more memory structures configured to: a) store a recursive memory of input signals past, and b) allow for at least one time series prediction of a response.

In certain method embodiments, the method is a time-lagged feed forward method for predicting analyte levels in a sample or a subject in need thereof.

In certain method embodiments, the method further includes providing one or more memory structures in both the input and hidden layers.

In certain method embodiments, the method can further include providing one or more memory structures included in the output layer.

In certain method embodiments, the input layer accepts and stores at least one memory of a current input signal and at least one memory of a previous input signal, and wherein the input layer stores a record of the input signals past and provides a usable history of previous input data to allow at least one time series prediction.

In certain method embodiments, the method includes the step of predicting a complete vector of predicted values with a respective time vector t, wherein the complete vector of predicted values comprises all predicted values up to n minutes of the desired predictive window, and wherein the respective time vector t is adaptive to accommodate a defined sampling rate ($\Delta t$).

In certain method embodiments, the hidden layers have one or more $Y_{hiddeni}$ neurons/processing elements configured for providing an alternative representation of input data, and, optionally, configured for simplifying the input data to a specific range of values in order to enhance a training/learning process of the method.

In certain method embodiments, the $Y_{hiddeni}$ hidden layer neurons/processing elements are configured to utilize one or more transfer functions selected from but not limited to: hyperbolic tangent, sigmoid, and linear functions.

In certain method embodiments, may contain at least one hidden layer contains at least one memory structures $MD_{hiddeni}$ configured to: store a record of the input signals past, and provide a usable history of previous input data to allow for at least one time series prediction.

In certain method embodiments, the output layer has one or more $Y_{output}$ processing elements/neurons configured for implementing at least one transfer function.

In certain method embodiments, at least one transfer function is implemented in the hidden layer.

In certain method embodiments, at least one $Y_{output}$ processing element is configured to output a predicted response in a format of a desired output of the method.

In certain method embodiments, the number of neurons/processing elements ($Y_{output}$) in the output layer is the same as a desired number of outputs of the method.

In certain method embodiments, the method includes the step of training via a backpropagation algorithm having one or more elements $BP^{layer}$ in the method help facilitate a training process, where "layer" is the layer(s) defined as "input", "hiddeni" and "output" to which the $BP^{layer}$ corresponds.

In certain method embodiments, one or more BPlayer elements derive a relative error at their input which is to be back propagated to any processing elements which precede them in the method.

In certain method embodiments, the back propagation of errors is completed as an error and is presented at the output of each BPlayer element, wherein each BPlayer element is charged with calculating gradient information associated with calculating weights for minimization of total error in the method.

In certain method embodiments, optimal weights for minimization of error are obtained via a gradient descent algorithm performed within each BPlayer element.

In certain method embodiments, the optimal weights calculated via the gradient descent algorithm are changed in the elements and synapses/connections between a current and next layer of the method, whereby the weighted inputs are summed at the input of each neuron/processing element.

In certain method embodiments, the gradient descent algorithm calculates the optimal weights for minimization of total error in the method by specifying a step size in which the algorithm iterates to determine a local minimum.

In certain method embodiments, the neural network is configured to utilize momentum to aid in the gradient descent algorithm, wherein momentum provides the gradient descent algorithm inertia such that the algorithm continues to move along the average estimate for down in its search for a local minimum.

In certain method embodiments, the method includes the step of training via a batch training approach.

In certain method embodiments, network weights are updated after/during each epoch, wherein the epoch comprises a single cycle/pass through a dataset.

In certain method embodiments, the method includes the step of stopping training if a calculated mean squared error was less than a specified threshold or after n epochs.

In certain method embodiments, the method includes the step of training via an optimization technique.

In certain method embodiments, the optimization technique comprises a genetic algorithm configured to minimize the number of processing elements (neurons) and inputs into the method.

In certain method embodiments, the genetic algorithm is configured to determine which inputs have an impact on predictions and to minimize various interconnections between neurons in the method.

In certain method embodiments, the genetic algorithm determines one or more optimum values for step-size and momentum to minimize the time required for weight optimization and training via a gradient search algorithm.

In certain method embodiments, the method includes the step of pre-processing data, wherein N inputs in the input layer are pre-processed to decrease the time needed for training/executing the method and to increase the predictive accuracy of the method.

In certain method embodiments, the method includes pre-processing of data such that new inputs experienced by the method are taken into account, and model weights and normalization of input values are modified as the new input data is presented to the method.

In certain method embodiments, the pre-processing of inputs is completed using one or more algorithmic techniques selected from but not limited to: normalization and weighting.

In certain method embodiments, the method includes the step of both real-time prediction and retrospective prediction.

In certain method embodiments, the method includes providing one or more support/post processing algorithms to modify a method predictive output such that an increased predictive accuracy is achieved.

In certain method embodiments, the method includes one or more support/post processing algorithms selected from but not limited to: an adaptive analyte threshold based rate of change (ROC) algorithm and input variable, or event, oriented trend analysis algorithm.

In certain method embodiments, the adaptive analyte threshold based ROC post processing algorithm is configured to track the ROC of analyte data presented to the method.

In certain method embodiments, wherein, based on a current analyte value and ROC of current and previous analyte values, if the n predicted analyte values do not correlate with the ROC, the predicted output of the method are modified via the post processing algorithm to increase predictive accuracy.

In certain embodiments, wherein the post processing includes an adaptive analyte threshold based ROC approach:

$$ROC(t) = \frac{(CGM_t - CGM_{t-1})}{\Delta t}, \qquad \text{Equation [1]}$$

wherein $CGM_t$ is the current real-time value, $CGM_{t-1}$ is the previous value, $\Delta t$ is the time duration between the two samples or sampling rate of a monitoring device, and ROC(t) is the real-time ROC, wherein, n predicted values generated are adjusted to coordinate with real-time ROC to enhance predictive accuracy via Equation [2], $$PREDICT_{mod} = PREDICT_{CGM} + W_{ROC} \cdot ROC \cdot \Delta t \qquad \text{Equation [2]},$$

wherein, $PREDICT_{CGM}$ is a vector of predicted CGM values with length n, $W_{ROC}$ is a vector of length n of weights for weighting ROC values based on the current real-time value (threshold), ROCpredict is a vector of ROC values of length n estimated based on best linear, or nonlinear model of real-time ROC, $\Delta t$ is a time duration between the two samples or a sampling rate, and $PREDICT_{mod}$ is a vector of modified (post-processed) predictions to increase accuracy based on trends in real-time ROC.

In certain method embodiments, the method includes the step of providing one or more input variables oriented trend analysis post processing algorithms which are configured to analyze one or more predicted outputs of the method for one or more expected trends in predicted analyte values based on previous and current input data presented to the method.

In certain method embodiments, at least one trend is quantifiable and is programmed into the method to gauge if predictions generated by the method are accurate.

In certain method embodiments, if predictions digress from an expected trend, appropriate post-processing is completed to modify predictions and enhance predictive accuracy.

In certain method embodiments, if the expected trend does not occur in n predicted values, then the post processing algorithm will modify the output to increase predictive accuracy.

In certain method embodiments, one or more of the input signals past comprise: physiologic, emotional, lifestyle, medication, and nutritional factors, factors documented during the course of the subject's normal everyday life, or during treatment, stay in intensive care or other supervised setting, and medical records.

In certain method embodiments, at least one trend includes: an increase in glucose followed by a decrease to normal levels if a medication dosage was sufficient.

In certain method embodiments, the method further includes the step of prospectively and retrospectively gauging at least one change and/or at least one occurrence of one or more input factors and a corresponding effect of the factors on at least one prediction.

In certain method embodiments, the method includes a retrospective and/or prospective iterative therapeutic and/or educational tool for determination of effect of at least one input variable.

In certain method embodiments, at least one input variable comprises one or more of: analyte concentration, analyte levels, analyte states and outcomes.

In certain method embodiments, the method further includes the step of predicting one or more outputs selected from: glucose levels, including discrete and/or CGM values; glucose states, including classified ranges of glucose values; glycated hemoglobin A92C values, mortality, morbidities, and complications; at a point in time n minutes in the future, when applicable, in real-time and retrospectively.

In certain method embodiments, the method includes the step of administration of insulin/medication dosage administration, and intelligent therapy guidance, in an integrated or stand-alone manner.

In certain method embodiments, the method includes the step of predicting glucose n minutes ahead of time and to forecast all glucose levels over a predetermined time in the future.

In certain method embodiments, the method includes the step of using multiple inputs for prediction.

In certain method embodiments, the multiple inputs include one or more of: time, meter glucose readings, nutritional intake, daily activities, lifestyle factors, emotional states, medication intake and patient medical records.

In certain method embodiments, the method includes the step of using multiple inputs for prediction utilizing continuous glucose monitoring (CGM) data.

In certain method embodiments, the method includes the step of using multiple inputs for prediction utilizing meter blood glucose data.

In certain method embodiments, the method includes the step of training via a backpropagation neural network training modality/algorithm.

In certain method embodiments, the method includes the step of training via a batch training method.

In certain method embodiments, the method includes the step of training via an optimization technique.

In certain method embodiments, the method includes the step of real-time and retrospective predicting.

In certain method embodiments, the predictive capabilities of the neural network include pre-processing and support/post processing algorithms to modify neural network predictive output such that an increased predictive accuracy is achieved.

In certain embodiments, the algorithm is selected from: adaptive glycemic threshold based rate of change (ROC) algorithms, and input variable (event) oriented trend analysis algorithms.

In certain method embodiments, the glycemic threshold based rate of change (ROC) post processing algorithm track real-time ROC of glucose data presented to the neural network.

In certain method embodiments, the neural network includes one or more post processing algorithms configured to analyze predicted output of the neural network for expected trends in predicted glucose values based on previous and current input data presented to the neural network.

In certain method embodiments, the method includes the step of predicting future glucose values and/or outcomes which provides a user with advanced knowledge in real-time of possible unwanted glycemic excursions and outcomes.

In certain method embodiments, the method allows a user to select an amount of time to predict values ahead of time, and to display one or more of: current, previous history, and predicted output in real-time.

In certain method embodiments, the method includes providing one or more alerts and/or alarms to alert a user of potential and present unwanted glucose values and outcomes.

In certain method embodiments, the method includes the step of calculating error in prediction and to retrain or reformulate at least one model weight for increased accuracy.

In certain method embodiments, the method includes the step of alerting a user when predictive accuracy is below a desirable error threshold, thereby allowing the user to interpret results using clinical judgment cautiously.

In certain method embodiments, the method includes the step of retrospectively analyzing an effect of medication and/or other input data on future predicted values such that appropriate modifications to therapy can be made.

In certain method embodiments, the method includes the step of providing a user with type I or type II diabetes with therapeutic guidance such that the user can make modifications to avoid unwanted glucose values and outcomes.

In certain method embodiments, the method includes the step of monitoring patients in a hospital/critical care setting with elevated glucose.

In certain method embodiments, the method includes the step of monitoring real-time and predicted glucose in critical care and hospital patients, to alert, guide, and optimize glycemic control in critical care patients with lack of glycemic control.

In certain method embodiments, the method includes the step of gauging performance and status of military personnel on the battlefield.

In certain method embodiments, the method includes the step of being implemented in a closed loop system or a semi-closed loop system.

In certain method embodiments, the method includes the step of predicting glucose and outcomes n minutes in the future, as well as suggesting therapeutic changes in medication for mitigation and prevention of unwanted glycemic excursions and outcomes.

In certain method embodiments, the method includes allowing a user to choose whether to accept any therapeutic recommendations given by the semi-closed loop system implementing the multifunctional neural network model, or modify the recommendations to adjust medication delivery.

In certain method embodiments, the method includes the step of automatically integrating with a medication delivery system to allow changes in therapy desired by a user to be implemented in real-time.

In certain method embodiments, the method includes the step of functioning as a closed loop system to automatically deliver medication and other therapeutic changes to maintain desired glucose values and outcomes.

In certain method embodiments, the method includes the step of being configured to be used with one or more of: computers, smartphones, pocket PCs/PDAs, laptop/tablet PCS and PCs.

In certain method embodiments, the method includes the step of being integrated for used with one or more of: current and future glucose monitoring, insulin infusion technologies for prediction of glucose, outcomes, medication dosages/lifestyle changes needed for improved glycemic control, variables pertinent to optimization of glycemic control and outcome in patients with diabetes (type I and II), trauma/hospital/cardio-thoracic surgical patients/critical care, military personnel, and other patients with elevated glucose and lack of optimized glycemic control.

In certain method embodiments, the method includes the step of prospectively and retrospectively gauging a change and/or occurrence of at least one input factor and/or its corresponding effect on predictions.

In certain method embodiments, one or more of the step are performed using a computerized system.

In another broad aspect, there is provided herein a computer program product comprising a computer useable medium having computer program logic for enabling at least one processor in a computer system to predict in real-time, the computer program logic comprising a neural network having: i) an input layer designed to accept N inputs; ii) one or more "i" hidden layers, iii) an output layer; iv) at least one neuron "Ylayer" within each layer, where "layer" is the layer defined as "input", "hiddeni" or "output"; and, v) one or more memory structures configured to: a) store a recursive memory of input signals past, and b) allow for at least one time series prediction of a response.

In certain embodiments, the computer program product includes the neural network as described herein. Further in certain embodiments, such neural network is a time-lagged feed forward neural network for predicting analyte levels in a sample or a subject in need thereof.

In another broad aspect, there is provided herein a computer system for predicting complete vector of predicted values with a respective time vector t, comprising: i) an input module that designed to accept N inputs; ii) one or more "i" hidden layer modules; iii) an output layer module; iv) at least one neuron "$Y_{layer}$" module within each layer, where "layer" is the layer defined as "input", "hiddeni" or "output"; and, v) one or more memory structure modules configured to: a) store a recursive memory of input signals past, and b) allow for at least one time series prediction of a response. In certain embodiments the complete vector of predicted values comprises all predicted values up to n minutes desired predictive window, and wherein the respective time vector t is adaptive to accommodate a defined sampling rate ($\Delta t$).

It is to be understood that the word "analyte" can comprise different materials and can be one or more of: naturally occurring, artificial, metabolites, and/or reaction products.

Non-limiting examples of such include: glucose; blood and/or urine components; proteins; amino acids; hormones; cholesterol; viruses; toxins; antibodies; antigens; vitamins; imaging contrast agents; illegal drugs; pharmaceutical compositions; and steroids. For ease of explanation, the following description will be directed to "glucose" as the "analyte."

In a broad aspect, there is provided herein a system for forecasting and predicting glucose concentration and glycemic states, for prediction of medication dosages for maintaining normal glucose concentration, and for predicting outcome in various applications.

The system described herein is easily adaptable to accept multiple inputs which can then be used to further train the model for improved performance.

The system described herein can be utilized as a standalone intelligent therapy recommendation model/system/software, semi-closed loop system, and as a supportive algorithm for a closed loop system or stand-alone closed loop controller.

The system disclosed herein can also be easily configured for predicting within a user defined time window and can be customized/updated in real-time.

The system described herein can be useful in various applications including, but not limited to: type I/II diabetes, trauma patients with elevated glucose, cardio-thoracic surgical patients, and critically ill/critical care patients and/or military personnel.

The system described herein can facilitate enhanced glucose control as well as potentially reduce complications/morbidities associated with the various venues and applications as described herein.

The system described herein can be utilized to provide real-time intelligent therapy recommendation via utilization/ integration in various medical devices or technology such as cell phones, smartphones, personal computers, laptop, pocket PCs/PDAs, etc, closed-loop and semi-closed loop diabetic therapy systems, real-time hospital/critical care/cardio-thoracic surgical patients trauma therapy systems, models for prediction of outcome in urgent care.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT(S)

Figure 1:
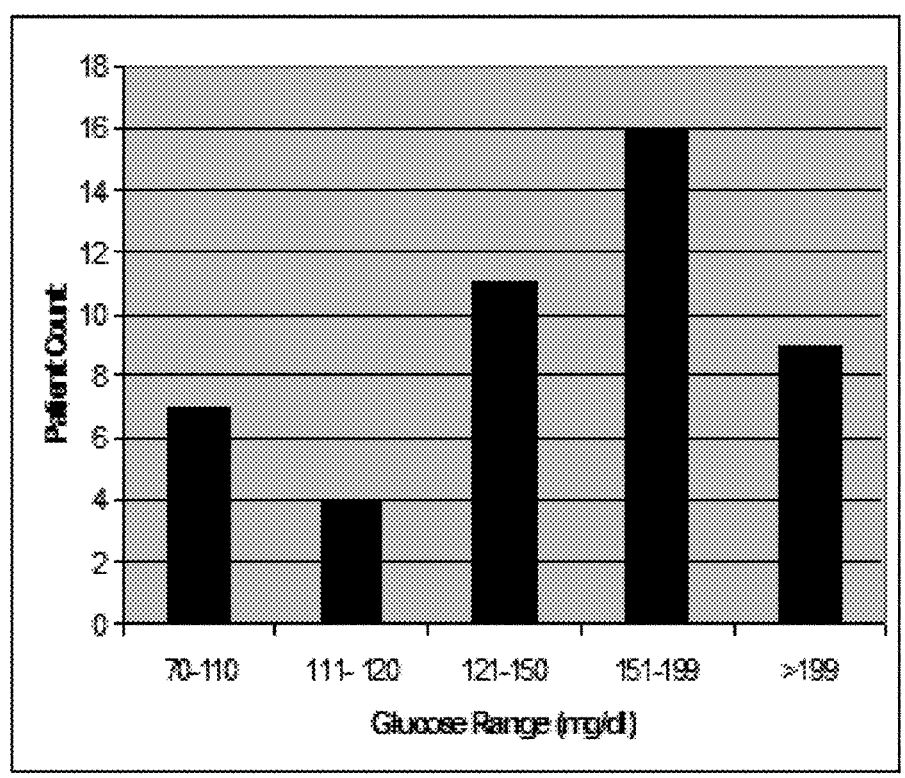
FIG. 1. Graph showing initial glucose levels for 50 Level 1 trauma patients upon arrival to the ICU FIG. 2. Graph showing glucose variability in a single trauma patient (Apr. 23-May 1, 2006).
Figure 2:
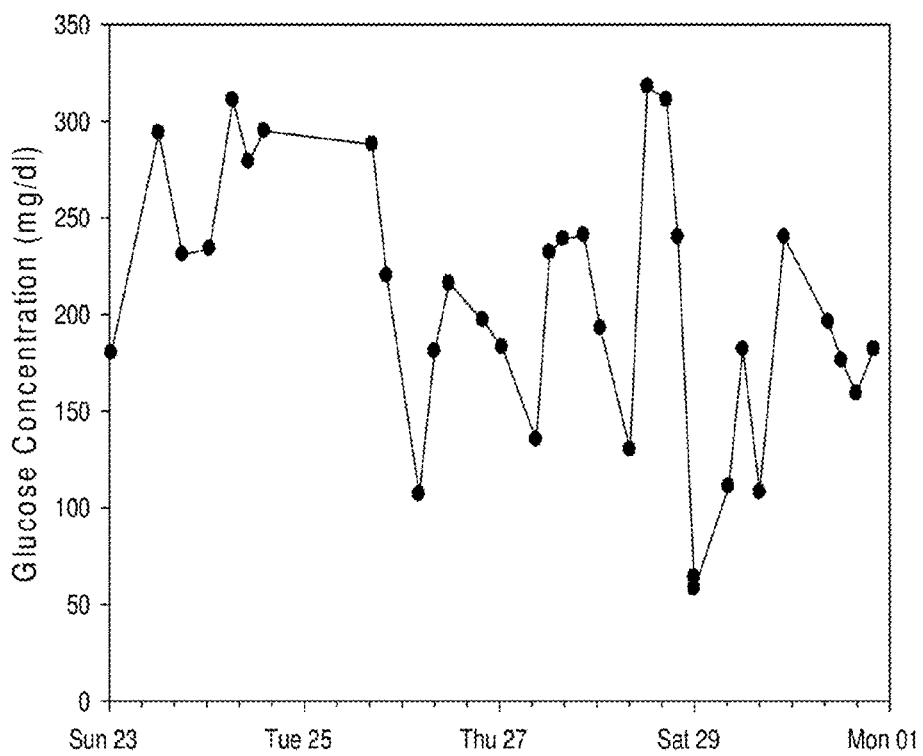

In a broad aspect, there is provided herein an improved system for predicting glucose levels and insulin/medication dosages.

In a particular aspect, there is provided herein a multifunctional neural network for prediction of glycemic levels, glycemic states, medication dosages, and pertinent physiologic/clinical outcomes.

The usage of the multifunctional neural network for the prediction of specific glucose concentration values, as well as specific glycemic states, allows for enhanced accuracy and enhanced intelligent therapeutic assistance/guidance.

Also, the existence of multiple outputs makes it possible to verify accuracy of predictions if the outputs coincide with each other.

The pre-processing of input data (which is variable dependent on application and venue for glycemic prediction) is presented to the neural network model via various algorithmic techniques in order to enhance the accuracy of the neural network. Non-limiting examples of algorithmic techniques include: normalization and weighting.

The presence of neural network output post processing algorithms are utilized to enhance the predictive accuracy during a time of decreased model accuracy.

The potential for neural network re-training also gives the system a unique and supported construct in the event model weight optimization is needed when new data combinations and results are experienced.

The present invention described herein also provides for the integration of real-time CGM data as an input and an output of the neural network. The usage of a time lagged feed forward neural network (or an adaptation thereof) allows the usage of both previous and current real-time CGM data in order to predict future real-time glycemic data trends. The multi-input customization also allows for real-time data-logging of variables which may be predictors of future glycemia.

In another aspect, there is provided herein an intelligent therapy recommendation/semi-closed loop insulin infusion system that can be used in many different types of applications and/or venues. Such a system provides a method for enhanced blood glucose control, which is the goal of all diabetes technology, and also important in critical care medicine: trauma, cardio-thoracic surgical patients.

In another aspect, there is provided herein an intelligent therapy recommendation/semi-closed loop insulin infusion system that can accomplish one or more of: prediction of glucose and glycemic states, insulin dosage administration, and intelligent therapy guidance, in an integrated manner.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

EXAMPLES

Figures 3, 4:
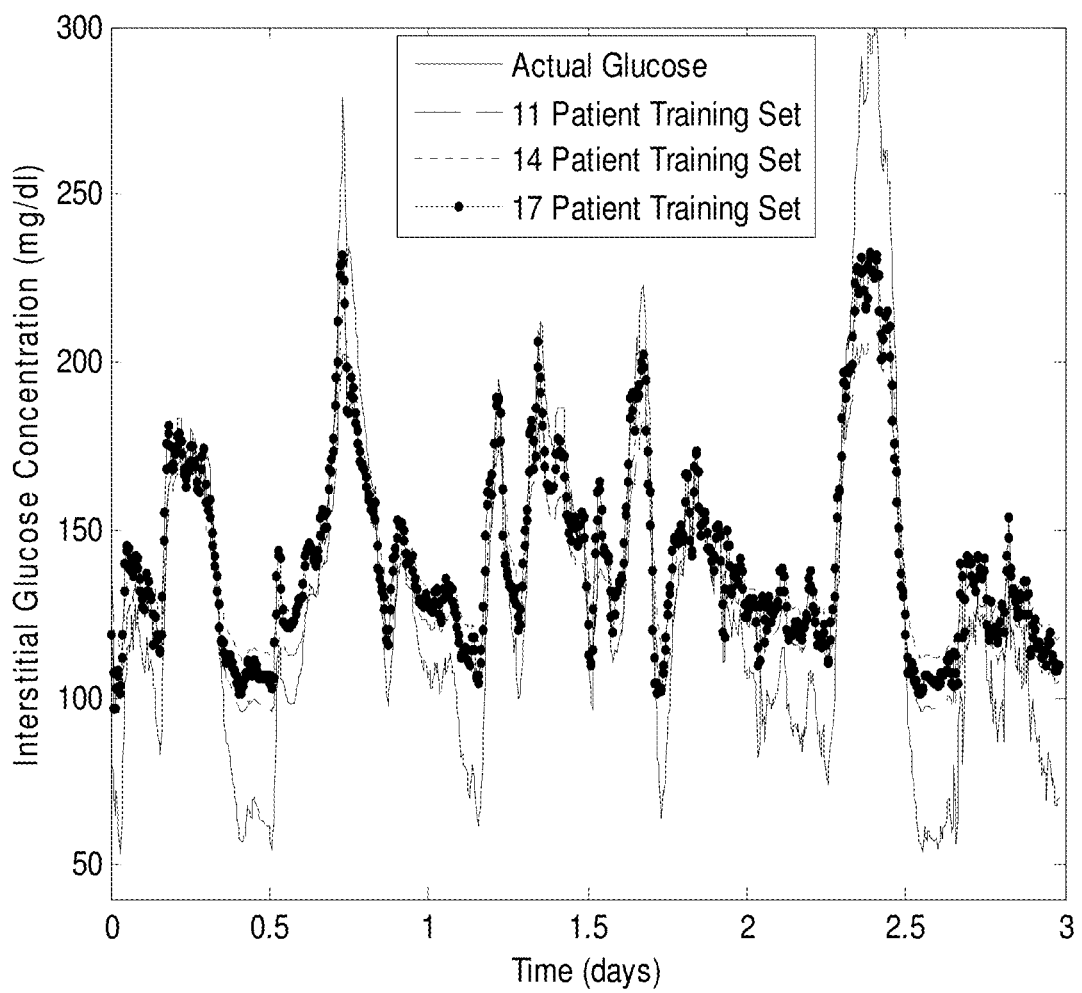
FIG. 3. Graph showing neural network prediction of unseen data: variation of training set length for a 100 minute predictive window. * An error of 11-21% exists in the Medtronic CGMS system relative to serum glucose levels [35].
FIG. 4: Table 1. Performance Analysis on Unseen Data: Variation of Training Set Length (100 minute Predictive Window).

The prediction of glucose values in an unseen diabetic patient (i.e., patient not used in neural network training set) using the multifunctional neural network with a predictive window of 100 minutes is demonstrated in FIG. 3. The number of patient data records used for training the neural network model was varied and the error (mean absolute difference percent (MAD %)) between the neural network predicted glycemic concentrations and actual CGM data is reported ranging from 18.7-25.8% in Table 1 (FIG. 4).

Figures 5, 6:
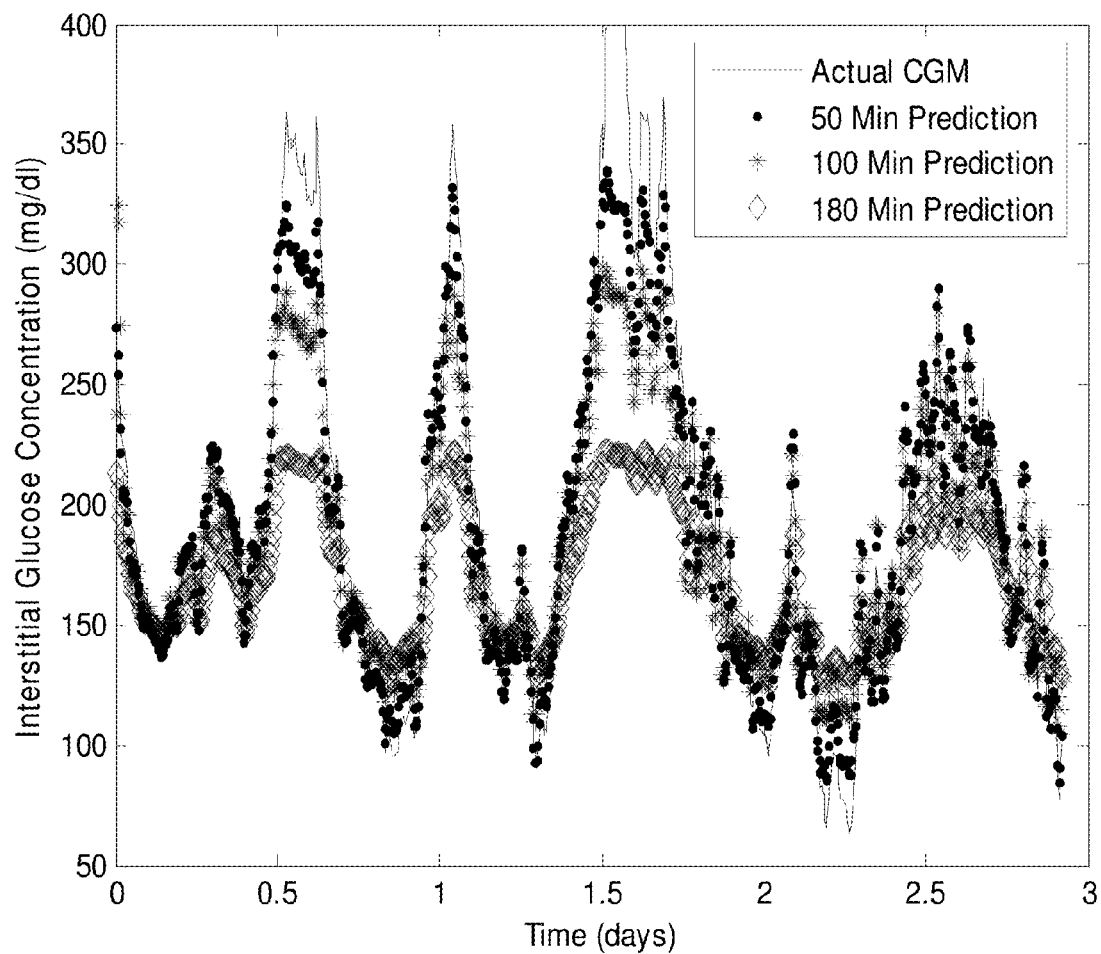
FIG. 5. Graph Neural Network Performance: Predictive Window Variation (Unseen Data) * An error of 11-21% exists in the Medtronic CGMS System relative to serum glucose levels [35]
FIG. 6. Table 2. Performance Analysis: Unseen Data With Predictive Window Variation.

The prediction of glucose values in an unseen diabetic patient (i.e., patient not used in neural network training set and model development) using the multifunctional neural network is demonstrated in FIG. 5. The predictive window was varied for the neural network models from 50-180 minutes. The error (mean absolute difference percent (MAD %)) between neural network predicted glycemic concentrations and actual CGM data is reported ranging from 6.7-18.9% in Table 2 (FIG. 6).

In one embodiment, the neural network system can be constructed to generate predictions in simulated real-time setting. For example, the neural network system can generate predictions upon reception of CGM data in real-time every five minutes. An analysis of this real-time system development and model integration with CGM in patients with insulin dependent diabetes mellitus, and critical care patients is included in FIGS. 7-10.

Figure 7:
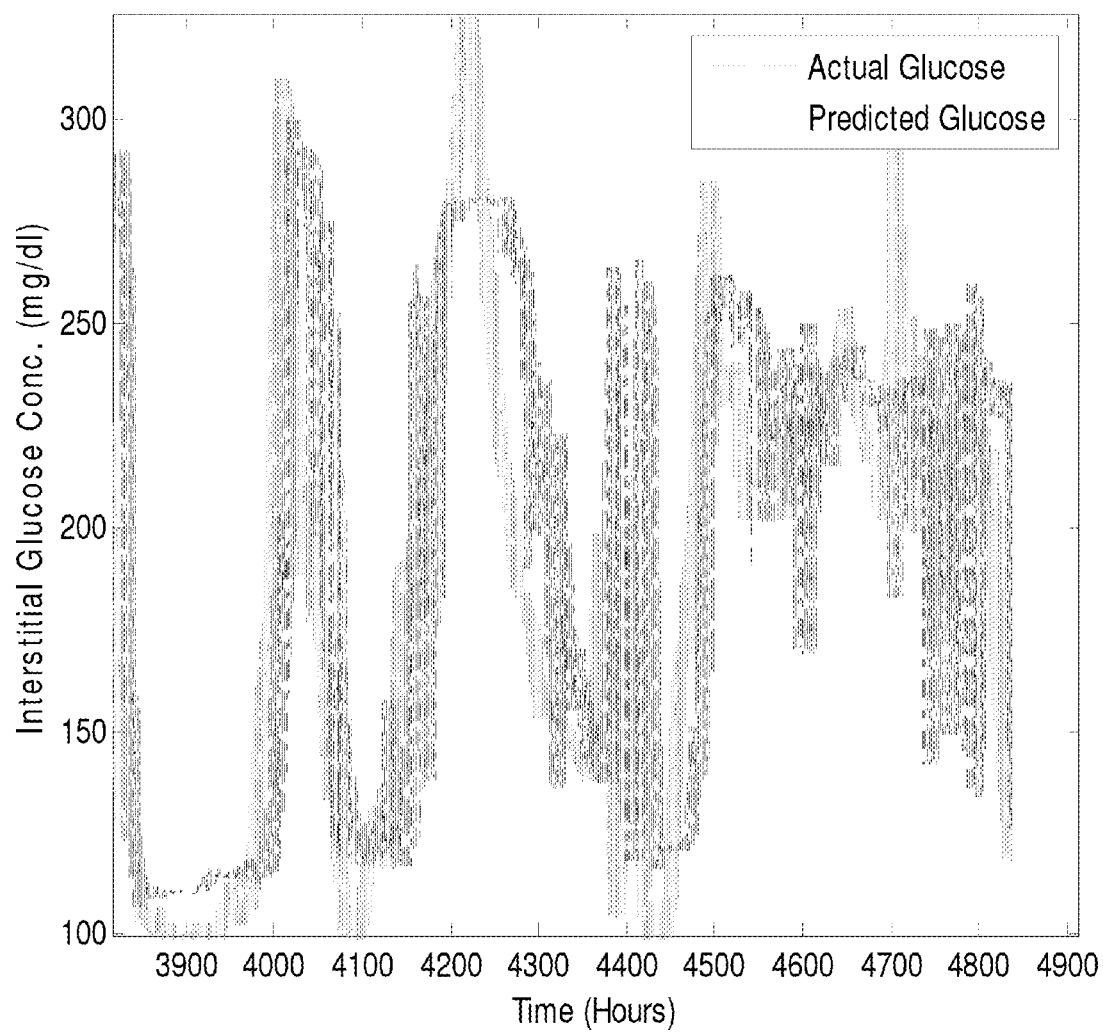
FIG. 7. Prediction of Glucose (using a forecast window of 75 minutes) in Simulated Real-Time Setting on Patients with Insulin Dependent Diabetes Mellitus FIG. 8. Clarke Error Grid Analysis of simulated real-time prediction of glucose (using a forecast window of 75 minutes) in patients with insulin dependent diabetes mellitus.

FIG. 7 demonstrates the predictive capabilities (using a forecast window of 75 minutes) in a simulated real-time setting in patients with insulin dependent diabetes mellitus. The simulated real-time prediction of glucose was performed on unseen data (i.e., data not used in initial model development). The utilization of unseen data provides insight to the application of the neural network system in a real patient in a real-world situation. FIG. 7 demonstrates that the predictions generated track the trends in the glucose effectively.

Figure 8:
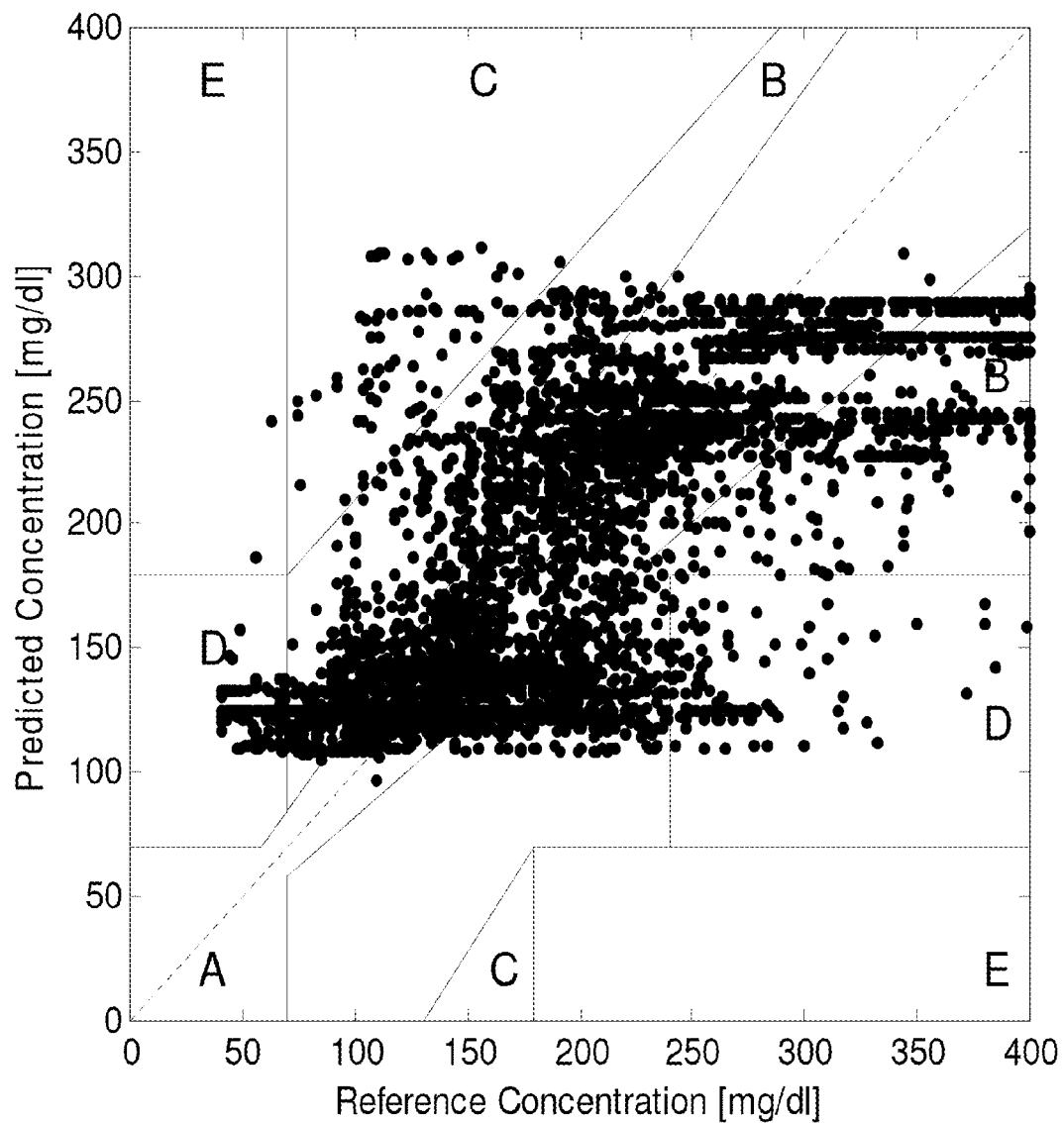

FIG. 8 is the Clarke Error Grid Analysis (CEGA) of predictions generated using 322.5 hours of unseen CGM data in diabetes patients. CEGA revealed that 90.4% of the predictions were clinically acceptable and fell within regions A and B of the error grid. In addition, further analysis of the predictive results demonstrate that 77.5% of the hyperglycemic glucose values (≥180 mg/dl) were predicted and 82.0% of the normal glucose values (>70 and <180 mg/dl) were predicted.

Figure 9:
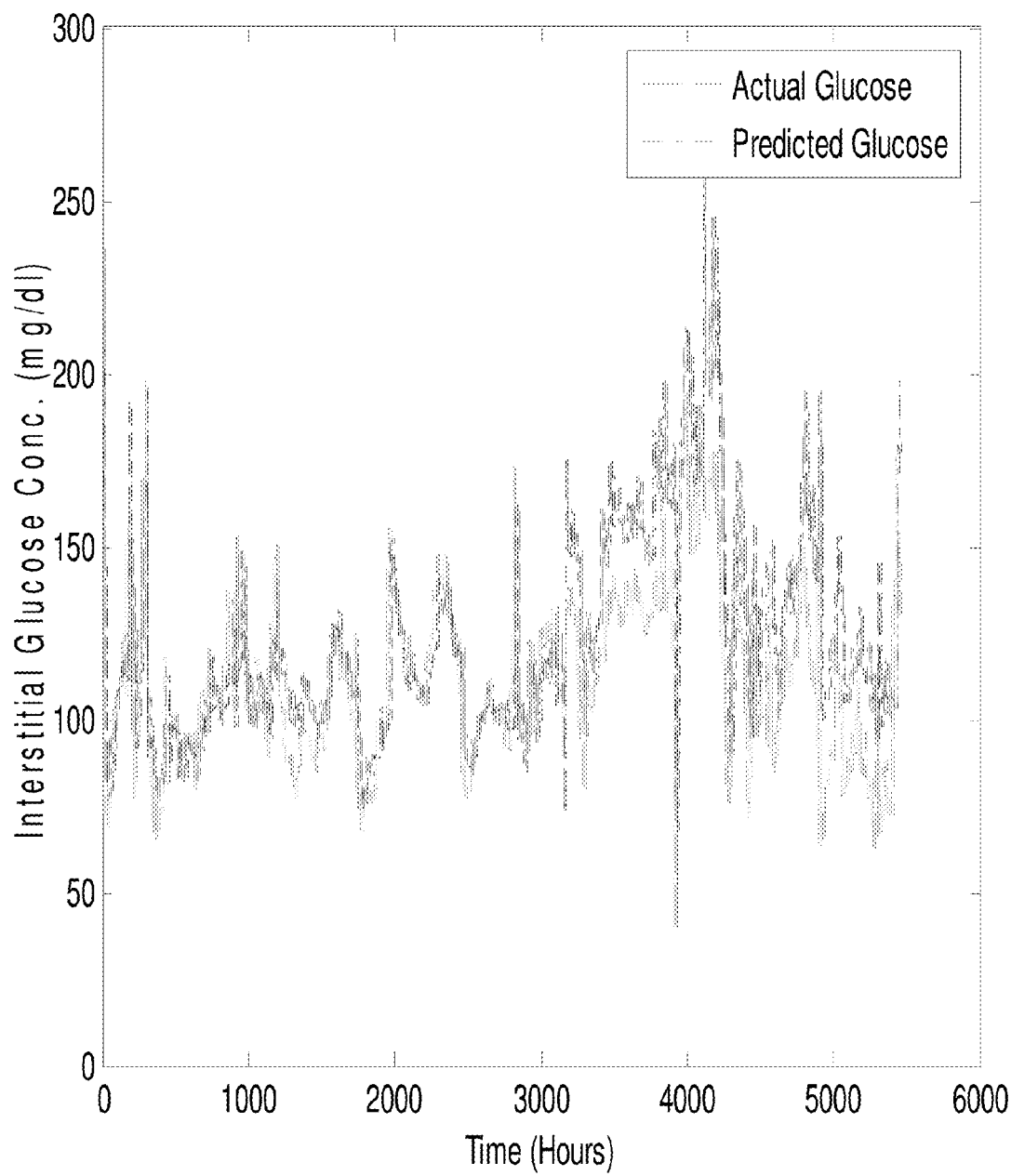
FIG. 9. Prediction of Glucose (using a forecast window of 75 minutes) in Simulated Real-Time Setting in 4 Critical Care Patients (trauma and cardio-thoracic surgical intervention)

FIG. 9 demonstrates the predictive capabilities (using a forecast window of 75 minutes) in a simulated real-time setting in 4 critical care patients with trauma or cardiac surgical intervention. The simulated real-time prediction of glucose was performed on unseen data (i.e., data not used in initial model development). The utilization of unseen data provides insight to the application of the neural network system in a real patient in a real-world situation. FIG. 9 also demonstrates that the predictions generated track the trends in the glucose effectively.

Figure 10:
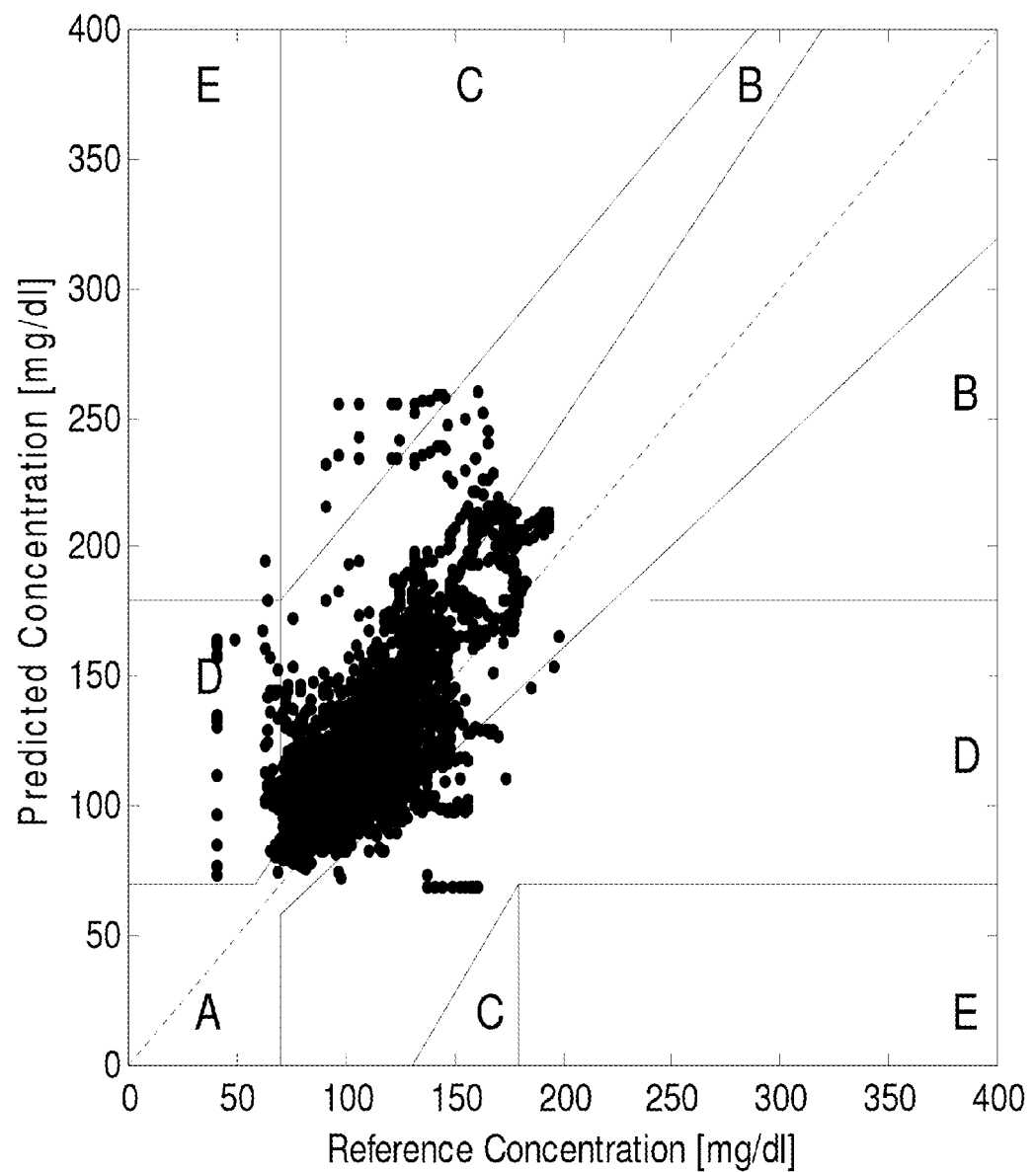
FIG. 10. Clarke Error Grid Analysis of simulated real-time prediction of glucose (using a forecast window of 75 minutes) in 4 critical care patients.

FIG. 10 is the Clarke Error Grid Analysis (CEGA) of predictions generated using 364.1 hours of unseen CGM data in critical care patients. CEGA revealed that 97.9% of the predictions were clinically acceptable and fell within regions A and B of the error grid. In addition, further analysis of the predictive results demonstrate that 84.0% of the hyperglycemic glucose values (≥150 mg/dl) were predicted and 86.3% of the normal glucose values (>70 and <150 mg/dl) were predicted.

Multi-Functional Neural Network

The multifunctional neural network has various applications in such diverse fields as: type I and type II diabetes, hospital/critical care/trauma patients/cardio-thoracic surgical patients, and military personnel.

The neural network is "multifunctional", in that there are X desired/predicted outputs of the neural network. The neural network is designed to predict glucose levels (discrete or CGM values), and glucose states (classified ranges of glucose values) n minutes in the future (in real-time and retrospectively).

In addition to these predicted outputs, the neural network can be utilized to predict outputs relevant to the target application of the neural network. For example, the neural network, when applied to glucose prediction in diabetes, can be configured to predict glycated hemoglobin AlC values which are indicative of the degree of glycemic control a diabetic patient has.

In another example, in the case of trauma and military personnel, the neural network can be configured to predict mortality, morbidities, complications and the like. The neural network is designed to accept N inputs. It is to be understood that the N inputs can include a variety of the factors which may affect glucose/analyte levels. These factors include, but are not limited to: physiologic, emotional, lifestyle, medication, and nutritional factors. In the case of hospital/trauma/critical care/cardio-thoracic surgical patients, inputs to the neural network include factors documented during the course of the patient stay in their intensive care or medical records. Thus, the neural network model is designed with multiple layers which consist of input, hidden, and desired layers.

Neural Network Architecture

Figure 11:
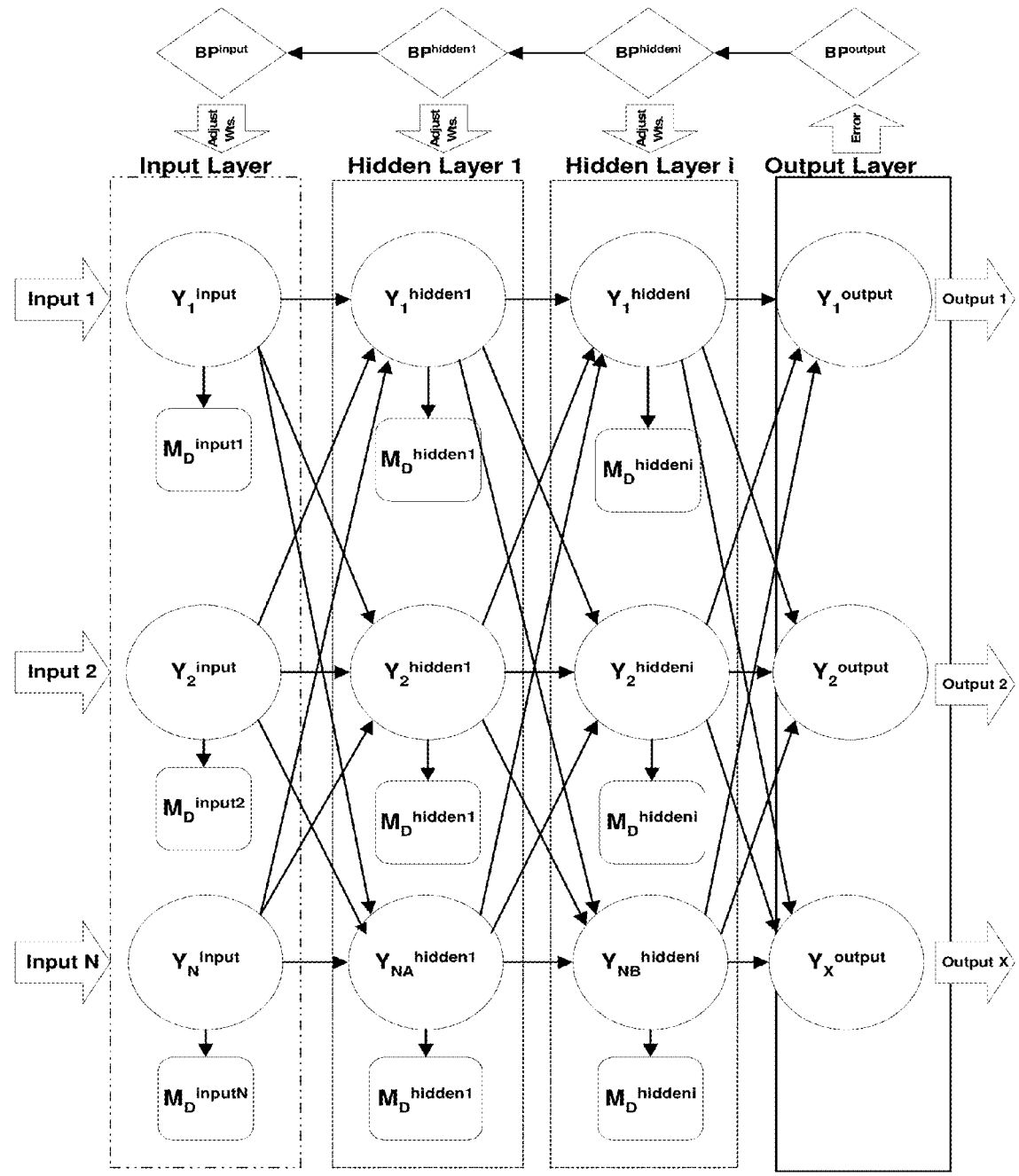
FIG. 11. Schematic illustration of a Neural Network Architecture and Information Flow.

The neural network is a time-lagged feed forward neural network and is fabricated via a multi-layer design. FIG. 11 is a graphical representation of the neural network architecture and information flow.

The neural network generally includes: an input layer, one or more I hidden layers, and an output layer. The number of neurons $Y^{layer}$ (where layer is the layer of the neural network defined as "input", "hidden$_i$", and "output") in each layer is variable, depending on the application of the neural network. The existence of memory structures within the neural network thus function to store a recursive memory of the input signals past. This is integral to allow for time series prediction of a response and allows for the determining how far in the future one wants to make such prediction.

These memory structures are included in the design of both the input and hidden layers of the neural network, but also may be included in the output layer (not shown). The number of inputs (input signal's past) stored in the memory structure (i.e., the size, or depth, of the memory structure) is $M_D$.

The input layer of the neural network is designed to accept N inputs. The input layer functions to accept and store a memory of both the current and the previous input signals. The input layer serves as a memory structure to store a record of the input signals past and to provide a usable history of previous input data to allow time series prediction. These inputs may include, but are not limited to: physiologic, emotional, lifestyle, medication, and nutritional factors. In the case of hospital/trauma/critical care/cardio-thoracic surgical patients, inputs to the neural network can include the previous factors in addition to those factors documented during the course of the patient stay in their intensive care or medical records.

The neural network also has i hidden layers. These hidden layers have $Y^{hidden}_i$ neurons/processing elements which utilize various transfer functions to provide an alternative representation of input data and can simplify the input data to a specific range of values in order to enhance the training/learning process of the neural network.

The hidden layer neurons/processing elements can utilize transfer functions such as, but not limited to: hyperbolic tangent, sigmoid, and linear functions. As with the input layer, the hidden layer can also contain various memory structures of size $M_D^{hidden}{}_i$. These memory structures serve to store a record of the input signals past and to provide a usable history of previous input data to allow for time series prediction.

The output layer has $Y^{output}$ processing elements/neurons for implementing a transfer function such as, but not limited to, those implemented in the hidden layer. These processing elements function to output the predicted response of the neural network in the format of the desired output of the neural network. The number of neurons/processing elements ($Y^{output}$) in the output layer is the same as the desired number of outputs of the neural network (e.g., various variables being predicted) and varies based on the application of the neural network.

The various layers of the neural network are connected via synapses. These synapses (solid black in FIG. 11) interconnect all of the elements within the neural network and provide a means for data to flow through the neural network. The number of synapses included in the neural network architecture is dependent upon the number of processing elements in each layer, and the number of layers in each neural network design. This is variable depending on end use application and can also be modified during subsequent model development and optimization.

Neural Network Training

The neural network can be trained via a backpropagtion algorithm or other suitable training algorithm. The existence of elements $BP^{layer}$ (where layer is the layer(s) defined as "input", "hidden$_i$", and "output" of which the $BP^{layer}$ corresponds) in the neural network help facilitate the training process. The $BP^{layer}$ elements derive a relative error at their input which is to be back propagated to any processing elements which precede them in the neural network design. Back propagation of errors is completed as an error is presented at the output of each $BP^{layer}$ element, and each $BP^{layer}$ element is charged with calculating the gradient information associated with calculating weights for minimization of total error in the neural network.

Optimal weights for minimization of error in the predictive model are obtained via a gradient descent algorithm performed within each $BP^{layer}$ element. The weights which are calculated via the gradient descent algorithm are then changed in the elements and synapses/connections between the current and next layer of the neural network. Thus, the weighted inputs are summed at the input of each neuron/processing element.

This gradient descent algorithm calculates the optimal weights for minimization of total error in the neural network. This is accomplished via specifying a step size in which the algorithm iterates to determine the local minimum. In addition to step size, the neural network also utilizes momentum to aid in the gradient descent algorithm. Momentum is a method which provides the gradient descent algorithm inertia such that the algorithm continues to move along the average estimate for down in its search for a local minimum.

The neural network can be trained via batch training (e.g., network weights are updated after each epoch (single cycle/pass through the dataset)), but other training configurations may be implemented. Also, the neural network can be configured to stop training if the mean squared error was less than a specified threshold or after n epochs.

The neural network can be trained using various optimization techniques. For example, optimization of the neural network can be completed via a genetic algorithm or other suitable optimization methods. [39,40] In certain embodiments, optimization via a genetic algorithm can be used in order to minimize the number of processing elements (neurons) and inputs into the neural network. The genetic algorithm effectively determines which inputs have an impact on predictions and minimizes the various interconnections between neurons in the neural network. The genetic algorithm also determines the optimum values for step-size and momentum to minimize the time required for weight optimization and training via the gradient search algorithm discussed above.

Neural Network Data Pre-Processing

The N inputs (depending upon application) in the input layer of the neural network can be preprocessed via an algorithmic technique or normalization method, which can then decrease the time needed for training/executing the neural network model, as well as, increase the predictive accuracy of the neural network. The pre-processing of data also includes pre-processing of data such that new inputs experienced by the neural network model are taken into account and model weights and normalization of input values are modified as the new input data is presented to the neural network model. In one non-limiting example, pre-processing of inputs to the neural network can be completed via multiple algorithm techniques such as but not limited to: normalization, weighting and the like.

Neural Network Output Post-Processing

The multifunctional neural network is configurable for both real-time prediction and retrospective prediction. To improve the predictive capabilities of the neural network, one or more support/post processing algorithms are included in order to modify the neural network predictive output such that an increased predictive accuracy is achieved. Non-limiting examples of suitable supporting algorithms can include: glycemic threshold based rate of change (ROC) algorithms, and input variable (event) oriented trend analysis algorithms.

In certain embodiments, the glycemic threshold based ROC post processing algorithm will track the ROC of glucose data presented to the neural network. Based on the current glucose value and ROC of the current and previous glucose values, if the n predicted glucose values do not correlate with the ROC, the predicted output of the neural network will be modified via the post processing algorithm to increase predictive accuracy.

In one embodiment, the glycemic threshold based ROC post-processing algorithm may be applied according to Equations 1-2 below.

Equation 1 is the calculation of the real-time rate of change (ROC)) of glucose, where $CGM_t$ is the current real-time glucose value, $CGM_{t-1}$ is the previous glucose value, and $\Delta t$ is the time duration between the two glucose samples or sampling rate of the glucose monitoring device.

Utilizing the real-time ROC(t), the n predicted values generated by the model (based on predictive window selected and implemented by user) will be adjusted to coordinate with real-time ROC of glucose to enhance predictive accuracy via Equation 2.

$PREDICT_{CGM}$ is a vector of predicted CGM values with length n, $W_{ROC}$ is a vector of length n of weights for weighting ROC values based on the current real-time glucose value (glycemic threshold), $ROC_{predict}$ a vector of ROC values of length n estimated based on best linear, or nonlinear model of real-time glucose ROC, $\Delta t$ is the time duration between the two glucose samples or sampling rate of the glucose monitoring device, and $PREDICT_{mod}$ is a vector of modified (post-processed) predictions to increase model accuracy based on trends in real-time glucose ROC.

This post processing algorithm is adaptive in that the weights in $W_{ROC}$ can be modified/adapted (via various mathematical approaches) such that error of the neural network model is minimized.

NOTE: All vectors which are multiplied are multiplied element by element.

$$ROC(t) = \frac{(CGM_t - CGM_{t-1})}{\Delta t} \qquad \text{[Equation 1]}$$

$$PREDICT_{mod} = PREDICT_{CGM} + W_{ROC} \cdot ROC \cdot \Delta t \qquad \text{[Equation 2]}$$

The input variable (event) oriented trend analysis post processing algorithms will function to analyze the predicted output of the neural network for expected "trends" in predicted glucose values based on previous and current input data presented to the neural network. Based on inputs presented to the neural network (which is application specific) various expected trends may be determined.

For example, if nutritional intake occurred in a patient with diabetes the expectation is that glucose would increase in absence of insulin. If insulin was taken before the nutritional intake, an expected trend would be an increase in glucose followed by a decrease to normal levels if insulin dosage was sufficient. This trend is quantifiable and can be programmed into the neural network system to gauge if predictions generated by the neural network are indeed accurate. If predictions digress from such an expected trend, appropriate post-processing may be completed to modify predictions and enhance predictive accuracy. If the expected trend does not occur in the n predicted glucose values, then the post processing algorithm will modify the neural network output to increase predictive accuracy.

Examples of Uses

There are multiple applications and embodiments of which the multifunctional neural network model may be implemented, nonlimiting examples of which are described herein.

Real-Time Intelligent Therapy Assistive System

The multifunctional neural network model can be implemented as a real-time intelligent therapy assistive system in many different applications. Non-limiting examples of such applications include: the hospital/critical care setting, individual patient medical devices, semi-closed loop and closed loop insulin infusion devices, military battleground applications, and the like. The neural network can predict future glucose values, outcomes, etc. which will allow patients, care-givers, and related personnel advanced knowledge of possible unwanted glycemic excursions and outcomes.

The real-time intelligent therapy assistive system can be configured to allow users to select the amount of time to predict values ahead of time, and will display the current, previous history, and predicted output in real-time. The system can be configured with alerts and alarms to alert users of potential and present unwanted glucose values and outcomes.

Such a system can be used in real-time or retrospectively to analyze the effect of medication and other input data (medication, nutritional intake, activity, stress levels, etc.) on future predicted values such that appropriate modifications to therapy can be made.

The system has the ability to accept real-time inputs and therefore output the effect of the newly entered/acquired inputs on future predictive results.

Such a system can provide patients with type I or type II diabetes a means of therapeutic guidance such that they can make modifications to medication, lifestyle, etc. to avoid unwanted glucose values and outcomes.

Additionally, such a system is useful when applied for patients in the hospital/critical care setting with elevated glucose as there is a correlation with an increased mortality/morbidity rate in such patients. The real-time therapy assistive system can alert patients and caregivers of potential and present unwanted glycemic excursions and outcomes such that preventive measures may be taken beforehand.

Furthermore, a real-time therapy assistive system can provide a means to gauge performance and status of military personnel on the battlefield. Given injuries to military personnel, the real-time system can predict glucose values and whether the outcome for the injured military personnel is warranted for immediate or future evacuation. Performance of the military personnel can also be gauged using such a predictive system.

Semi-Closed Loop and Closed Loop Systems

The multifunctional neural network can be implemented in a closed and/or semi-closed loop system in patients with type I diabetes (personal medical device) and hospital/critical care patients (hospital/personal medical device) with elevated glucose.

Given inputs to the closed and/or semi-closed loop system, such system can be modified to predict glucose and outcomes n minutes in the future as well as suggest therapeutic changes in medication for mitigation and prevention of unwanted glycemic excursions and outcomes. The user/patient/care providers can choose to accept the therapeutic recommendations given by the semi-closed loop system implementing the multifunctional neural network, or modify the recommendations to adjust a medication delivery. Such system can be automatically integrated with the medication delivery system to allow changes in therapy desired by the user/caregiver to be implemented in real-time.

The glucose levels predicted by the system along with relevant insulin delivery specifications for each patient (insulin sensitivity, insulin delivered, active insulin in body, etc.) can be input to a separate controller implementing an algorithmic/neural network structure for estimation of insulin required for maintaining a normal glucose concentration. This insulin delivery estimation can be automatically instantiated via communication to an insulin infusion device (closed loop) and/or displayed to the patient/caregiver for their interpretation and or assessment of the systems recommendations (intelligent therapy direction/semi-closed loop system).

In the case of critical care, trauma, and cardio-thoracic patients in the hospital, a bedside monitor (for intelligent therapy direction) can be configured to communicate with continuous glucose monitoring or glucose meter and the caregiver can see real-time CGM data, as well as select predictive/forecast window to see where glucose will be n minutes ahead of time.

Figure 12:
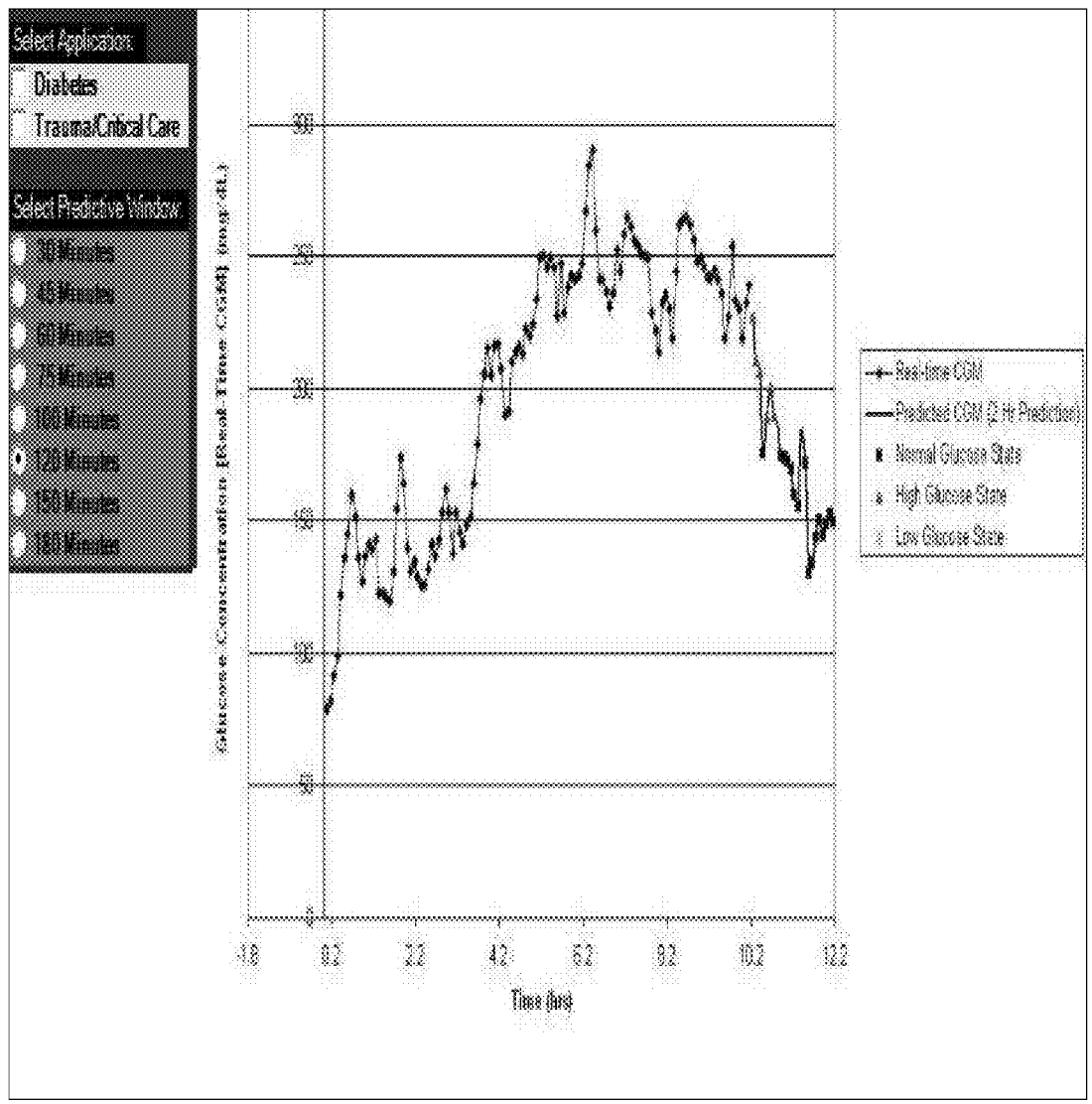
FIG. 12. Real-time model execution in user interface of medical device or bedside monitor for intelligent therapy direction and/or automation.

The system can be configured to alert/alarm patients of pending or anticipated occurrences of hypoglycemia and hyperglycemia. If ideal model accuracy is achieved, predictions can then be used for automated insulin delivery via either a closed loop or semi-closed loop system. A similar closed and/or semi-closed loop system can be utilized for patients with diabetes as well. The system can show the patient past, real-time, and predicted CGM or glucose data based on the selection of forecast window by the patient and user. The system can be automatically connected with patient records, or data-logging devices to document relevant input data. One embodiment of a suitable layout of the predictive system is included in FIG. 12.

Coordination with Other Records

In addition to the applications outlined above, the bedside monitoring and predictive system can be configured to accept inputs from a medical record of which caregivers believe may impact future glucose. The caregiver can input these treatment parameters/inputs and see the effect on future glucose and modify treatment and or insulin delivery to accommodate for these factors.

Direct Delivery of Medication

Given predictive success the neural network, the neural network can also be modified to function as a closed loop system to automatically deliver medication and other therapeutic changes to maintain desired glucose values and outcomes.

Recordation of Predictive Activity

The system can keep track of predictive accuracy and report to the patient/user the utility of the predictions. If predictions are sufficiently accurate and within a certain threshold, the patient will be made aware that the predictions are likely accurate. In regions of decreased accuracy or when model accuracy is diminishing, the patient/user can be alerted to not use predictive results in therapy assessment and/or to retrain neural network or load pre-trained weights.

Versatility of Use in Different Settings/Venues

In certain embodiments, the neural network system can be utilized in one or more settings. For example, the system can be used in a universal setting (e.g., across a population of similar patients (e.g., diabetes, trauma with similar injuries, injury severity, etc), cardio-thoracic surgical patients, critical care patients, military injuries, etc.). In another example, the models can be used in a patient specific setting (e.g., using only data from a single patient for individualized neural network development and/or applications).

Integration with Other Devices

The neural network can be readily integrated with current technology such as, but not limited to: retrospective and real-time continuous glucose monitoring systems, insulin infusion pumps, personal computers, laptop computers, cellular phones, smart-phones, pocket PC devices, PDAs, etc.

In certain embodiments, the system can function as, but not be limited to: a software application, be applied via a microprocessor in a medical device, bed-side monitor/system, a network database/processing tool for therapeutic assistance/guidance (e.g., where data is sent and processed as needed).

Neural Network Optimization and Development

It is to be understood that modifications can be made to the neural network describe herein. For example, modification can be made to one or more of: the neural network architecture, inputs to the neural network, training methodologies, real-time applications and/or venues for prediction of glucose, pre-processing and/or post-processing algorithms, addition of additional algorithmic/model support for controlling and/or predicting of glucose and/or associated medication dosages for maintaining normal glycemic states, predicted outputs (e.g., variable dependent upon application and/or venue for prediction of glucose), utilization of predictive results for intelligent therapeutic direction, semi-closed loop and/or closed loop glycemic control, as well as the development and integration of the predictive models into current and newly developed technological innovations.

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A neural network system, comprising:
   i) an input layer configured to accept N input signals;
   ii) one or more "i" hidden layers,
   iii) at least one output layer;
   iv) at least one neuron "$Y^{layer}$" within each layer, where "layer" is the layer defined as "input", "hidden$_i$," or "output"; and,
   v) one or more memory structures configured to:
      a) store a recursive memory of input signals past, and
      b) allow for at least one time series prediction of a response,
   wherein the neural network is configured to include one or more input variables oriented trend analysis post processing algorithms which are configured to analyze one or more predicted outputs of the neural network system for one or more expected trends in predicted analyte values based on previous and current input data presented to the neural network system;
   wherein one or more support/post processing algorithms are included in order to modify the neural network system predictive output such that an increased predictive accuracy is achieved; and
   wherein the neural network includes a support/post processing algorithm comprising an input variable, or event, oriented trend analysis algorithm.

2. The neural network system of claim 1, wherein the neural network system is configured for both real-time prediction and retrospective prediction.

3. The neural network system of claim 2, wherein one or more support/post processing algorithms are included in order to modify the neural network system predictive output such that an increased predictive accuracy is achieved.

4. The neural network system of claim 3, wherein the neural network includes one or more support/post processing algorithms selected from: an adaptive analyte threshold based rate of change (ROC) algorithm and input variable, or event, oriented trend analysis algorithm.

5. The neural network system of claim 4, wherein the adaptive analyte threshold based ROC post processing algorithm is configured to track the ROC of analyte data presented to the neural network system.

6. The neural network system of claim 5, wherein, based on a current analyte value and ROC of current and previous analyte values, if the n predicted analyte values do not correlate with the ROC, the predicted output of the neural network system are modified via the post processing algorithm to increase predictive accuracy.

7. The network system of claim 1, wherein at least one trend is quantifiable and is programmed into the neural network system to gauge if predictions generated by the neural network system are accurate.

8. The neural network system of claim 7, wherein if predictions digress from an expected trend, appropriate post-processing is completed to modify predictions and enhance predictive accuracy.

9. The neural network system of claim 8, wherein if the expected trend does not occur in n predicted values, then the post processing algorithm will modify the neural network system output to increase predictive accuracy.

10. The neural network system of claim 1, configured to be a time-lagged feed forward neural network system for predicting analyte levels in a sample or a subject in need thereof.

11. The neural network of claim 1, wherein the network is configured for predicting analyte levels in a sample, the analyte comprising one or more of: artificial metabolites and/or reaction products.

12. The neural network system of claim 1, wherein the analyte comprises one or more of: blood and/or urine components proteins; amino acids; hormones; cholesterol;

viruses; toxins; antibodies; antigens; vitamins; imaging contrast agents; illegal drugs; pharmaceutical compositions; and steroids.

13. The neural network system of claim 1, wherein one or more of the input signals past comprise: emotional, lifestyle, and nutritional factors, factors documented during the course of the subject's normal everyday life, or during treatment, stay in intensive care or other supervised setting, and medical records.

14. The neural network system of claim 1, wherein the neural network system is configured to be used prospectively and retrospectively to gauge at least one change and/or at least one occurrence of one or more input factors and a corresponding effect of the factors on at least one prediction.

15. The neural network system of claim 1, wherein the neural network system is configured for use as a retrospective or prospective iterative therapeutic, or an educational tool for determination of effect of at least one input variable.

16. The neural network system of claim 1, wherein at least one input variable comprises one or more of: analyte concentration, analyte levels, analyte states and outcomes.

17. The neural network system of claim 1, for monitoring one or more of: type I and type II diabetes, hospital/critical care/trauma patients/cardio-thoracic surgical patients, and military personnel.

18. The neural network system of claim 1, configured for predicting one or more outputs selected from: glucose levels, including discrete and/or CGM values; glucose states, including classified ranges of glucose values; glycated hemoglobin A1C values, mortality, morbidities, and complications; at a point in time n minutes in the future, when applicable, in real-time and retrospectively.

19. The neural network system of claim 1, configured for providing administration of insulin/medication dosage administration, and intelligent therapy guidance, in an integrated or stand-alone manner.

20. A method for predicting analyte levels and medication dosages, comprising:
  i) providing a multifunctional neural network system of claim 1 for prediction of one or more of: analyte concentration values, analyte levels, analyte states, medication dosages, physiologic outcomes and clinical outcomes;
  ii) presenting pre-processing of input data to the neural network system;
  iii) providing a neural network system output post processing algorithm to enhance predictive accuracy during a time of decreased accuracy;
  iv) providing a capability for neural network system retraining for model weight optimization when new data combinations and results are experienced.

21. A neural network system, comprising:
  i) an input layer configured to accept N input signals;
  ii) one or more "i" hidden layers,
  iii) at least one output layer;
  iv) at least one neuron "$Y^{layer}$" within each layer, where "layer" is the layer defined as "input", "hidden$_i$," or "output"; and,
  v) one or more memory structures configured to:
    a) store a recursive memory of input signals past, and
    b) allow for at least one time series prediction of a response,
  wherein one or more memory structures are included in both the input and hidden layers,
  wherein the neural network is configured to include one or more input variables oriented trend analysis post processing algorithms which are configured to analyze one or more predicted outputs of the neural network system for one or more expected trends in predicted analyte values based on previous and current input data presented to the neural network system;
  wherein one or more support/post processing algorithms are included in order to modify the neural network system predictive output such that an increased predictive accuracy is achieved; and
  wherein the neural network includes a support/post processing algorithm comprising an input variable, or event, oriented trend analysis algorithm.

22. The neural network system of claim 21, wherein one or more of the input signals past comprise: emotional, lifestyle, and nutritional factors, factors documented during the course of the subject's normal everyday life, or during treatment, stay in intensive care or other supervised setting, and medical records.

23. The neural network system of claim 21, wherein one or more of the input signals past comprise: physiologic or medication factors.

24. A neural network system, comprising:
  i) an input layer configured to accept N input signals;
  ii) one or more "i" hidden layers,
  iii) at least one output layer;
  iv) at least one neuron "$Y^{layer}$" within each layer, where "layer" is the layer defined as "input", "hidden$_i$," or "output"; and,
  v) one or more memory structures configured to:
    a) store a recursive memory of input signals past, and
    b) allow for at least one time series prediction of a response;
  wherein the neural network system is configured for both real-time prediction and retrospective prediction;
  wherein one or more support/post processing algorithms are included in order to modify the neural network system predictive output such that an increased predictive accuracy is achieved;
  wherein the neural network includes one or more support/post processing algorithms selected from: an adaptive analyte threshold based rate of change (ROC) algorithm and input variable, or event, oriented trend analysis algorithm;
  wherein the adaptive analyte threshold based ROC post processing algorithm is configured to track the ROC of analyte data presented to the neural network system;
  wherein, based on a current analyte value and ROC of current and previous analyte values, if the n predicted analyte values do not correlate with the ROC, the predicted output of the neural network system are modified via the post processing algorithm to increase predictive accuracy; and
  wherein,
  n predicted values generated are adjusted to coordinate with real-time ROC to enhance predictive accuracy via Equation [2], $$\text{PREDICT}_{mod} = \text{PREDICT}_{CGM} + W_{ROC} \cdot \text{ROC}_{prediect} \cdot \Delta t \qquad \text{Equation[2]},$$

wherein,
  $\text{PREDICT}_{CGM}$ is a vector of predicted CGM values with length n, $W_{ROC}$ is a vector of length n of weights for weighting ROC values based-on the current real time value (threshold),
  $\text{ROC}_{predict}$ is a vector of ROC values of length n estimated based on best linear, or nonlinear model of real-time ROC,
  $\Delta t$ is a time duration between the two samples or a sampling rate, and PREDICT$_{mod}$ is a vector of modified (post-processed) predictions to increase accuracy based on trends in real-time ROC.

25. A neural network system, comprising:
i) an input layer configured to accept N input signals;
ii) one or more "i" hidden layers,
iii) at least one output layer;
iv) at least one neuron "Y$^{layer}$" within each layer, where "layer" is the layer defined as "input", "hidden$_i$," or "output"; and,
v) one or more memory structures configured to:
   a) store a recursive memory of input signals past, and
   b) allow for at least one time series prediction of a response;
wherein the neural network system is configured for both real-time prediction and retrospective prediction;
wherein one or more support/post processing algorithms are included in order to modify the neural network system predictive output such that an increased predictive accuracy is achieved;
wherein the neural network includes one or more support/post processing algorithms selected from: an adaptive analyte threshold based rate of change (ROC) algorithm and input variable, or event, oriented trend analysis algorithm;
wherein the adaptive analyte threshold based ROC post processing algorithm is configured to track the ROC of analyte data presented to the neural network system;
wherein, based on a current analyte value and ROC of current and previous analyte values, if the n predicted analyte values do not correlate with the ROC, the predicted output of the neural network system are modified via the post processing algorithm to increase predictive accuracy; and wherein the post processing includes an adaptive analyte threshold based ROC approach:

$$ROC(t) = \frac{(CGM_t - CGM_{t-1})}{\Delta t}, \quad \text{Equation [1]}$$

wherein
CGM$_t$ is the current real-time value,
CGM$_{t-1}$ is the previous value, $\Delta t$ is the time duration between the two samples or sampling rate of a monitoring device,
and
ROC(t) is the real-time ROC,
wherein,
n predicted values generated are adjusted to coordinate with real-time ROC to enhance predictive accuracy via Equation[2], $$\text{PREDICT}_{mod} = \text{PREDICT}_{CGM} + W_{ROC} \cdot \text{ROC}_{predict} \cdot \Delta t \quad \text{Equation[2]},$$

wherein,
PREDICT$_{CGM}$ is a vector of predicted CGM values with length n, W$_{ROC}$ is a vector of length n of weights for weighting ROC values based on the current real-time value (threshold),
ROC$_{predict}$ is a vector of ROC values of length n estimated based on best linear, or nonlinear model of real-time ROC,
$\Delta t$ is a time duration between the two samples or a sampling rate, and
PREDICT$_{mod}$ is a vector of modified (post-processed) predictions to increase accuracy based on trends in real-time ROC.

* * * * *

UNITED STATES PATENT AND TRADEMARK OFFICE
CERTIFICATE OF CORRECTION

| | | |
|---|---|---|
| PATENT NO. | : 9,076,107 B2 | |
| APPLICATION NO. | : 14/284975 | |
| DATED | : July 7, 2015 | |
| INVENTOR(S) | : Brent D. Cameron et al. | |

It is certified that error appears in the above-identified patent and that said Letters Patent is hereby corrected as shown below:

IN THE CLAIMS

Column 26, Claim 7, Line 46, after the insert --neural--.

Signed and Sealed this
Tenth Day of November, 2015

Michelle K. Lee
*Director of the United States Patent and Trademark Office*